United States Patent [19]

Ueda et al.

[11] Patent Number: 4,797,399

[45] Date of Patent: Jan. 10, 1989

[54] PIPERAZINE COMPOUNDS AND ANTITHROMBOTIC PHARMACEUTICAL COMPOSITION COMPRISING THE SAME

[75] Inventors: Ikuo Ueda; Masaaki Matsuo, both of Toyonaka; Kiyoshi Tsuji, Kishiwada; Hiroyuki Okumura, Ibaraki; Osamu Nakaguchi, Toyonaka, all of Japan

[73] Assignee: Fujisawa Pharmaceutical Co., Ltd., Osaka, Japan

[21] Appl. No.: 945,853

[22] Filed: Dec. 23, 1986

[30] Foreign Application Priority Data

Jan. 17, 1986 [GB] United Kingdom ................. 8601160

[51] Int. Cl.[4] ................... A61K 31/495; A61K 31/44; C07D 513/00; C07D 513/06

[52] U.S. Cl. ..................................... 514/253; 514/218; 540/575; 544/363; 544/368; 544/370; 544/373

[58] Field of Search ........................ 544/362, 368, 373; 514/253

[56] References Cited

U.S. PATENT DOCUMENTS

| | | | |
|---|---|---|---|
| 3,661,921 | 5/1972 | Umio et al. ......................... | 544/370 |
| 4,279,909 | 7/1981 | Takashima .......................... | 544/368 |

FOREIGN PATENT DOCUMENTS

| | | | |
|---|---|---|---|
| 10398 | 4/1980 | European Pat. Off. ............ | 514/253 |
| 4107515 | 8/1979 | Japan .................................. | 514/253 |
| 6015276 | 2/1981 | Japan .................................. | 514/253 |
| 6063972 | 5/1981 | Japan .................................. | 514/253 |
| 1238673 | 7/1971 | United Kingdom . | |
| 1270841 | 4/1972 | United Kingdom . | |

OTHER PUBLICATIONS

Chemical Abstracts, vol. 101, No. 19, Nov. 5, 1984, pp. 706-707, Ref. No. 171287G.

*Primary Examiner*—Donald G. Daus
*Assistant Examiner*—Cecilia Shen
*Attorney, Agent, or Firm*—Oblon, Fisher, Spivak, McClelland & Maier

[57] ABSTRACT

The present invention relates to N-containing fused heterocyclic compounds of the formula:

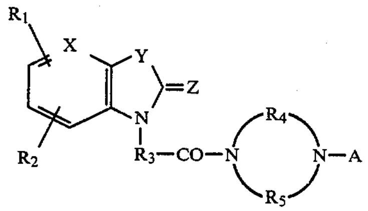

wherein $R_1$ and $R_2$ are each hydrogen, halogen, aryl, lower alkyl, halo (lower) alkyl or nitro,
$R_3$ is lower alkylene,
$R_4$ and $R_5$ are each lower alkylene,
X is CH or N,
Y is S, O, NH, C=N—OH or CO,
Z is O or NH, and
A is hydrogen, nitroso, amidino, a group of

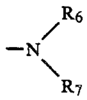

wherein $R_6$ and $R_7$ are each hydrogen, lower alkyl, acyl, or lower alkaneimidoyl which may be substituted with esterified carboxy, or a group of the formula:

$$—N=R_8,$$

wherein $R_8$ is lower alkylidene which may be substituted with aryl optionally substituted with suitable substituent(s).

The compounds are useful for treatment of thrombosis, inflammation, or allergic disease.

6 Claims, No Drawings

PIPERAZINE COMPOUNDS AND ANTITHROMBOTIC PHARMACEUTICAL COMPOSITION COMPRISING THE SAME

This invention relates to new N-containing fused heterocyclic compounds. More particularly, this invention relates to new N-containing fused heterocyclic compounds and pharmaceutically acceptable salts thereof which have pharmacologically activities, processes for preparation thereof, a pharmaceutical composition comprising the same and method of use thereof.

Accordingly, one object of this invention is to provide the new and useful N-containing fused heterocyclic compounds and pharmaceutically acceptable salts thereof.

Another object of this invention is to provide processes for preparation of the N-containing fused heterocyclic compounds and pharmaceutically acceptable salts thereof.

A further object of this invention is to provide a pharmaceutical composition comprising said N-containing fused heterocyclic compounds or a pharmaceutically acceptable salt thereof.

Still further object of this invention is to provide a method of using said N-containing fused heterocyclic compounds or a pharmaceutically acceptable salt thereof for therapeutic treatment of thrombosis, inflammation, or allergic disease, or as analgesic of human being and animals.

With regard to the state of the art in this field, 5-chloro-3-{[4-(2-hydroxyethyl)-1-piperazinyl]carbonylmethyl}-2-benzothiazolinone hydrochloride (generic name: Tiaramide hydrochloride) has been well known as anti-inflammatory drug.

The antithrombotic activity of said compound has also been known as described in The Japanese Journal of Pharmacology [Volume 30, Page 905-912, (1980)]. The object N-containing fused heterocyclic compounds of this invention are novel and represented by the following general formula [I]:

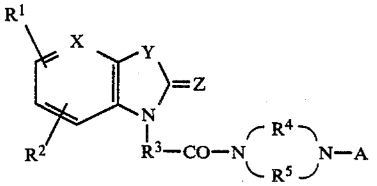

[I]

wherein $R^1$ and $R^2$ are each hydrogen, halogen, aryl, lower alkyl, halo(lower)alkyl or nitro, $R^3$ is lower alkylene, $R^4$ and $R^5$ are each lower alkylene, X is CH or N, Y is S, O, NH, C═N—OH or CO, Z is O or NH, and A is hydrogen, nitroso, amidino, a group of the formula:

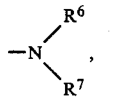

, wherein $R^6$ and $R^7$ are each hydrogen, lower alkyl, acyl, or lower alkaneimidoyl which may be substituted with esterified carboxy, or a group of the formula: —N═$R^8$ wherein $R^8$ is lower alkylidene which may be substitued with aryl optionally substituted with suitable substituent(s).

The object compound [I] of the present invention can be prepared by the following processes.

Process 1

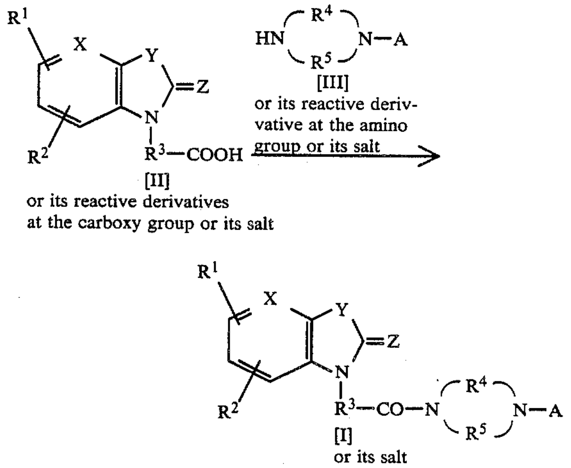

[II]
or its reactive derivatives at the carboxy group or its salt

[III]

[I]
or its salt

Process 2

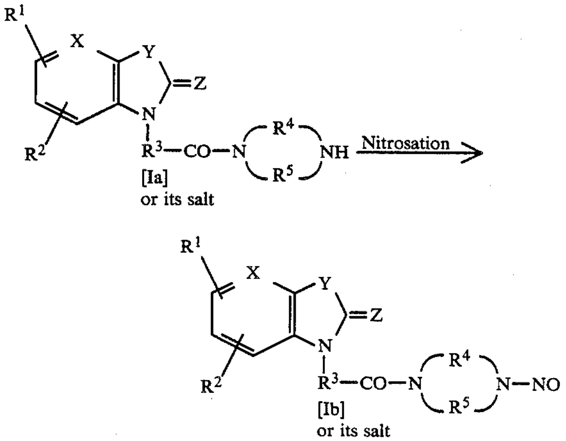

[Ia]
or its salt

[Ib]
or its salt

Process 3

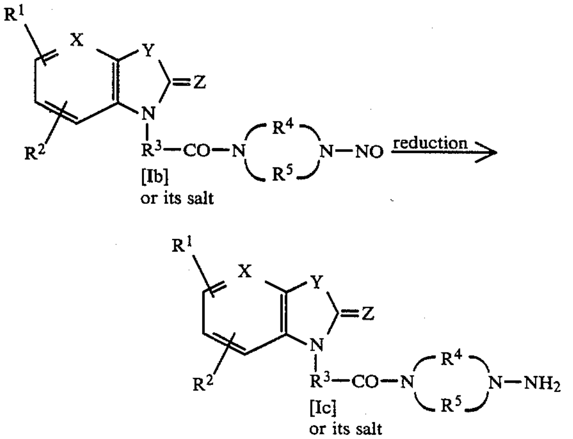

[Ib]
or its salt

[Ic]
or its salt

-continued
Process 4
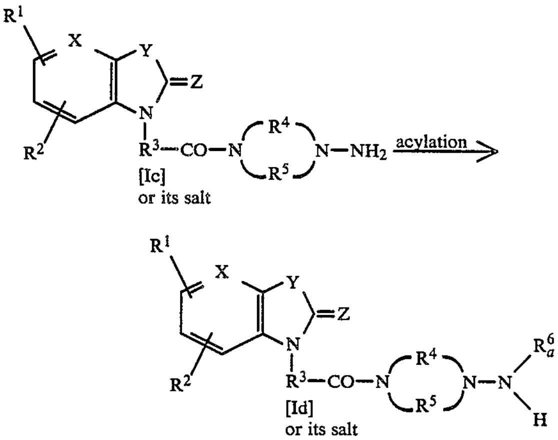
[Ic]
or its salt
[Id]
or its salt
Process 5
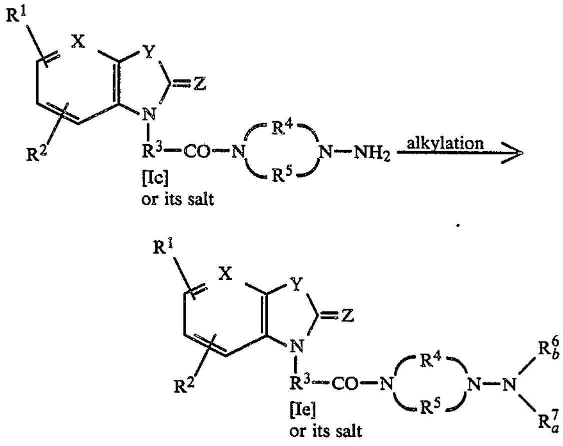
[Ic]
or its salt
[Ie]
or its salt
Process 6
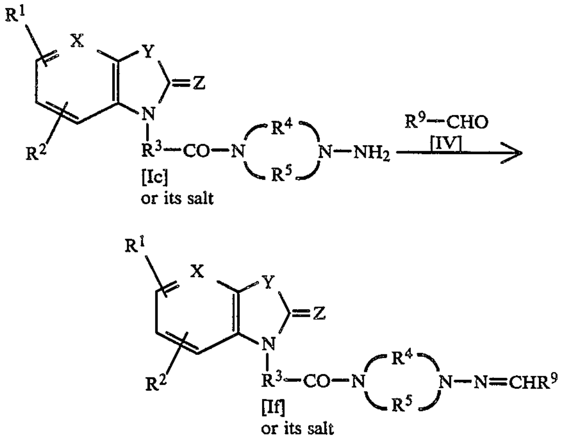
[Ic]
or its salt
[If]
or its salt
Process 7
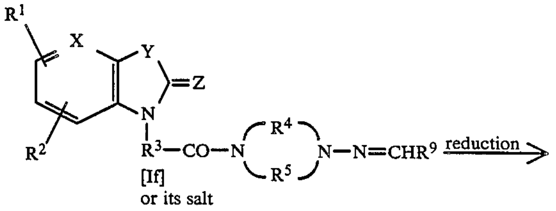
[If]
or its salt
-continued
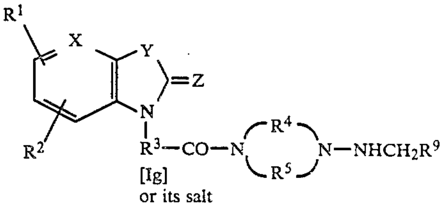
[Ig]
or its salt
Process 8
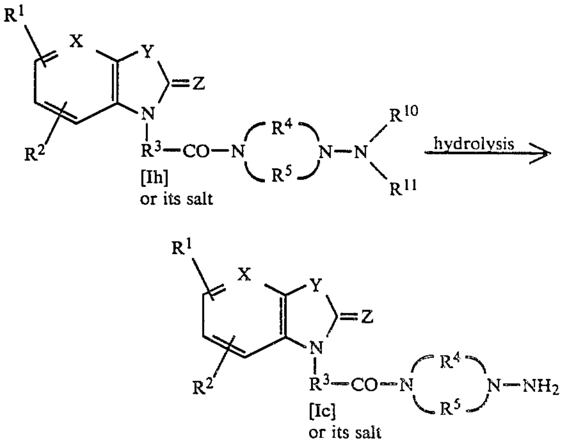
[Ih]
or its salt
[Ic]
or its salt
Process 9
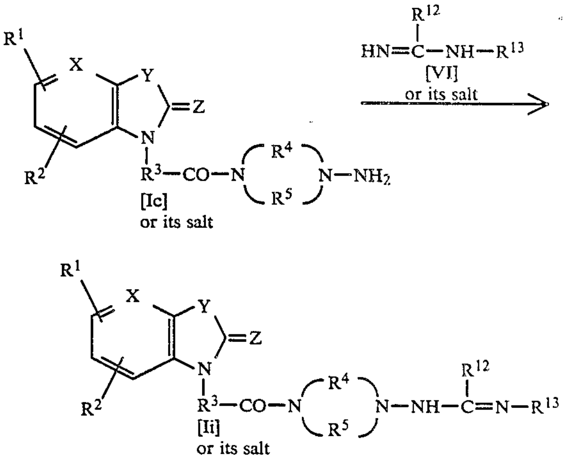
[Ic]
or its salt
[Ii]
or its salt
Process 10
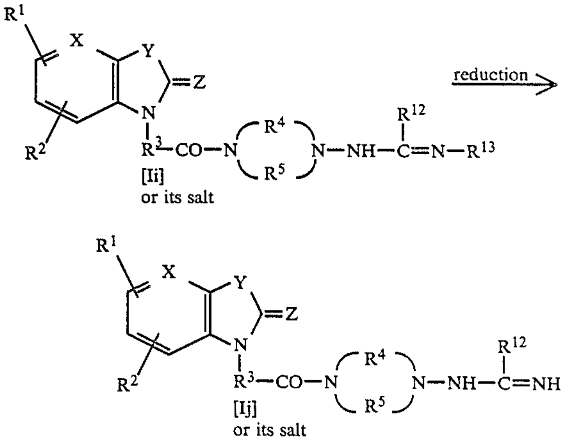
[Ii]
or its salt
[Ij]
or its salt -continued Process 11

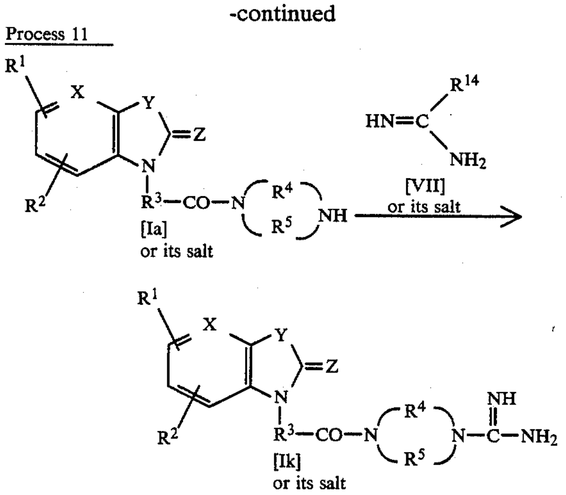

[Ia] or its salt

[Ik] or its salt wherein $R^1$, $R^2$, $R^3$, $R^4$, $R^5$, X, Y, Z and A are each as defined above, $R_a{}^6$ is acyl, $R_b{}^6$ is lower alkyl, $R_a{}^7$ is hydrogen or lower alkyl, $R^9$ is hydrogen, lower alkyl or aryl optionally substituted with suitable substituent(s), $R^{10}$ is acyl and $R^{11}$ is hydrogen or $R^{10}$ and $R^{11}$ are combined together to form a group of the formula: $=R^8$ wherein $R^8$ is as defined above, $R^{12}$ is lower alkyl, $R^{13}$ is esterified carboxy and $R^{14}$ is lower alkylthio.

In the above and subsequent description of the present specification, suitable examples and illustrations for the various definitions to be included within the scope of the invention are explained in detail as follows:

The term "lower" is intended to mean 1 to 6 carbon atom(s) unless otherwise indicated.

Suitable examples of the lower alkyl may be a straight or branched one such as methyl, ethyl, propyl, isopropyl, butyl, isobutyl, tert-butyl, pentyl, hexyl or the like.

Suitable example of "lower alkyl" moiety in the term "halo(lower)alkyl" and "lower alkylthio" can be referred to the ones as exemplified above.

Suitable example of "halo(lower)alkyl" may include "monohalo(lower)alkyl" [e.g. chloromethyl, bromomethyl fluoromethyl, etc.], "dihalo(lower)alkyl" [e.g. dichloromethyl, dibromomethyl, difluoromethyl, etc.] and "trihalo(lower)alkyl" [e.g. trichloromethyl, tribromomethyl, trifluoromethyl, trifluoroethyl, etc.] and the like.

Suitable examples of "lower alkoxy" may include methoxy, ethoxy, propoxy, isopropoxy, butoxy, isobutoxy, t-butoxy, pentyloxy, hexyloxy and the like.

Suitable examples of "halogen" may include chlorine, bromine, iodine and fluorine.

Suitable examples of "aryl" may include phenyl, tolyl, xylyl, cumenyl, naphtyl, and the like.

Suitable examples of "suitable substituent(s)" on said aryl may include hydroxy and the like, the number of which may be one or more.

Suitable examples of the lower alkylene group may be a straight or branched one such as methylene, ethylene, trimethylene, tetramethylene, pentamethylene, hexamethylene, propylene, methylethylene, ethylethylene, propylethylene, isopropylethylene, methylpentamethylene or the like.

Suitable examples of the lower alkylidene group may include methylene, ethylidene, propylidene, isopropylidene, butylidene, sec-butylidene, isobutylidene, hexylidene, isohexylidene and the like.

Suitable examples of acyl may include lower alkanoyl [e.g. formyl, acetyl, propionyl, valeryl, pivaloyl, etc.], lower alkoxycarbonyl [e.g. methoxycarbonyl, ethoxycarbonyl, propoxycarbonyl, isopropoxycarbonyl, butoxycarbonyl, t-butoxycarbonyl, pentyloxycarbonyl, hexyloxycarbonyl, etc.], lower alkanesulfonyl [e.g. methanesulfonyl, ethanesulfonyl, propanesulfonyl, butanesulfonyl, pentanesulfonyl, hexanesulfonyl, etc.], aroyl [e.g. benzoyl, naphthoyl, etc.] which may be substituted with halogen as exemplified above, arylcarbamoyl [e.g. phenylcarbamoyl, tolylcarbamoyl, etc.] which may be substituted with halogen as mentioned above, and the like.

Suitable esterified carboxy may include lower alkoxycarbonyl (e.g. methoxycarbonyl, ethoxycarbonyl, propoxycarbonyl, isopropoxycarbonyl, butoxycarbonyl, tert-butoxycarbonyl, etc.), mono(or di or tri)-phenyl(lower)alkoxycarbonyl which may have a nitro group (e.g. benzyloxycarbonyl, p-nitrobenzyloxycarbonyl, phenethyloxycarbonyl, benzhydryloxycarbonyl, trityloxycarbonyl, etc.), and the like.

Suitable examples of "lower alkaneimidoyl" may include acetimidoyl, propioimidoyl, etc.

Suitable pharmaceutically acceptable salts of the object compound [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], and the like.

In this respect, it is to be noted that the compounds [Ia] to [Ik] are included within the scope of the compoun [I], and accordingly the suitable salts of these compounds [Ia] to [Ik] are to be referred to those as exemplified for the object compound [I] in the above.

The processes for preparing the object compound [I] and salts thereof are explained in detail in the following.

PROCESS 1

The object compound [I] or its salt can be prepared by reacting the compound [II] or its reactive derivative at the carboxy group or its salt with the compound [III] or its reactive derivative at the amino group or its salt.

Suitable reactive derivative at the carboxy group of the compound [II] may include an acid halide, an acid anhydride, an activated amide, an activated ester and the like.

Suitable examples of such reactive derivatives may be acid chloride, an acid azide, a mixed acid anhydride with an acid such as substituted phosphoric acid [e.g. dialkylphosphoric acid, phenylphosphoric acid, etc.], aliphatic carboxylic acid [e.g. pivalic acid, acetic acid, trichloroacetic acid, etc.] or the like, a symmetrical acid anhydride, an activated amide with imidazole, triazole or dimethylpyrazole, an activated ester with N-hydroxysuccinimide, N-hydroxyphthalimide or 1-hydroxy-6-chlorobenzotriazole, and the like.

Suitable reactive derivatives at the amino group of the compound [III] include conventional ones used in amidation, for example, Schiff's base type imino or its tautomeric enamine type isomer formed by reaction of the compound [III] with a carbonyl compound, a silyl derivative formed by reaction of the compound [III] with a silyl compound such as trimethylsilylacetamide, bis(trimethylsilyl)acetamide or the like, a derivative formed by reaction of the compound [III] with phosphorus trichloride or phosgene, and the like.

This reaction may be carried out in the presence of a conventional condensing agent such as N,N-dicyclohexylcarbodiimide; phosphorus oxychloride; phosphorus trichloride; phosphorus pentachloride; thionyl chloride; oxalyl chloride; 1-(p-chlorobenzenesulfonyloxy)-6-chloro-1H-benzotriazole; so-called Vilsmeier reagent, for example (chloromethylene) dimethylammonium chloride produced by the reaction of dimethylformamide with thionyl chloride or phosgene, a compound produced by the reaction of dimethylformamide with phosphorus oxychloride, etc.; or the like.

This reaction is usually carried out in a conventional solvent such as water, methanol, ethanol, propanol, tetralin, tetrahydrofuran, dioxane, chloroform, toluene, dimethylformamide, dimethylsulfoxide, methylene chloride or any other organic solvent which does not adversely influence the reaction.

The reaction temperature is not critical, and the reaction is usually carried out under cooling, at ambient temperature or under warming.

PROCESS 2

The object compound [Ib] or its salt can be prepared by subjecting the compound [Ia] or its salt to nitrosation reaction.

The reaction can be carried out by reacting the compound [Ia] or its salt with nitrosating agent. Suitable nitrosating agent used in the present reaction may include nitrite compound [e.g. isoamyl nitrite, sodium nitrite, etc.] and the like.

This reaction is usually carried out in a conventional solvent such as methanol, ethanol, tetrahydrofuran, dioxane, methylene chloride, chloroform, benzene, dimethylformamide, dimethyl sulfoxide or any other organic solvent which does not adversely influence the reaction.

The reaction temperature is not critical, and the reaction can be carried out under cooling to warming.

PROCESS 3

The object compound [Ic] or its salt can be prepared by reducing the compound [Ib] or its salt.

The reaction including chemical reduction and catalytic reduction, may be carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent . A suitable solvent to be used may be water, alcohol [e.g. methanol, ethanol, propanol, etc.], acetonitrile or any other conventional organic solvent such as diethyl ether, dioxane, tetrahydrofuran, etc. or a mixture thereof. Additionally, the aforementioned liquid acids to be used in chemical reduction can also be used as a solvent.

The reaction is preferably carried out under cooling to warming.

PROCESS 4

The object compound [Id] or its salt can be prepared by acylating a compound [Ic] or its salt.

Suitable acylating agent to be used in this reaction includes an organic acid such as alkanoic acid [e.g. formic acid, acetic acid, propionic acid, etc.], arenecarboxylic acid (e.g. benzoic acid, toluenecarboxylic acid, etc.) which may have halogen, lower alkanesulfonic acid [e.g. methanesulfonic acid, etc.], arylisocyanate [e.g. phenylisocyanate, etc.] which may have halogen and its reactive derivative.

The suitable reactive derivative may be a conventional one such as an acid halide [e.g. acid chloride, acid bromide, etc.], an acid azide, an acid anhydride, an activated amide, an activated ester and the like.

When free acid is used as an acylating agent, the acylation reaction may preferably be conducted in the presence of a conventional condensing agent as mentioned above for Process 1.

The reaction can preferably be conducted in the presence of an organic or inorganic base such as alkali metal hydride [e.g. sodium hydride, potassium hydride, etc.], alkaline earth metal hydride [e.g. calcium hydride, magnesum hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal fluoride [e.g. potassium fluoride, cesium fluoride, etc.], alkali metal alkoxide [e.g. sodium methoxide, sodium ethoxide, potassium tert-butoxide, etc.], trialkylamine [e.g. trimethylamine, triethylamine, etc.], picoline, 1,5-diazabicyclo[4,3,0]non-5-ene, 1,4-diazabicyclo-82,2,2]octane, 1,5-diazabicyclo[5,4,0]undecene-5 or the like.

This reaction is usually carried out in a solvent which does not adversely influence the reaction such as water, methanol, ethanol, propanol, tetrahydrofuran, chloroform, dioxane, pyridine, methylene chloride or the like.

The reaction temperature is not critical and the reaction can be carried out under coolint to heating.

PROCESS 5

The compound [Ie] or its salt can be prepared by subjecting the compound [Ic] or its salt to alkylation reaction.

The alkylating agent to be used in the present alkylation reaction may include di(lower)alkyl sulfate [e.g. dimethyl sulfate, diethyl sulfate, etc.], diazo(lower)alkane [e.g. diazomethane, diazoethane, etc.], lower alkyl halide [e.g. methyl iodide, ethyl iodide, etc.], lower alkyl sulfonate [e.g. methyl p-toluenesulfonate, etc.], and the like.

The reaction using di(lower)alkyl sulfate, lower alkyl halide or lower alkyl sulfonate is usually carried out in a solvent such as water, acetone, ethanol, ether, dimethylformamide or any other solvent which does not adversely influence the reaction. The present reaction is preferably carried out in the presence of a base such as an inorganic base or an organic base as mentioned for Process 4. The reaction temperature is not critical and the reaction is usually carried out under cooling to heating around boiling point of the solvent.

The reaction using diazoalkane is usually carried out in a solvent such as ether, tetrahydrofuran or the like. The reaction temperature is not critical and the reaction is usually carried out under cooling or at ambient temperature.

The compound [Ie] or its salt can also be prepared by reacting the compound [Ic] or its salt with alkane aldehyde in the presence of reducing agent. Suitable alkane aldehyde may include formaldehyde, acetaldehyde, propionaldehyde and the like. Suitable reducing agent can be referred to the ones as mentioned above for Process 3. This reaction is usually carried out in a conventional solvent such as water, methanol, ethanol, propanol, tetralin, tetrahydrofuran, acetonitrile, dioxane, chloroform, toluene, dimethylformamide, dimethylsulfoxide or any other organic solvent which does not adversely influence the reaction.

The reaction temperature is not critical, and the reaction is usually carried out at ambient temperature or under cooling or warming.

PROCESS 6

The object compound [If] or its salt can be prepared by reacting the compound [Ic] or its salt with the compund [IV].

Suitable example of the compound [IV] can be referred to the ones as mentioned above for Process 5.

The reaction is usually carried out in a solvent. A suitable solvent to be used may be water, alcohol [e.g. methanol, ethanol, propanol, etc.], acetonitrile, or any other conventional organic solvent such as diethyl ether, dioxane, tetrahydrofuran, etc. or a mixture thereof.

The reaction is preferably carried out under somewhat milder conditions such as under cooling to warming.

PROCESS 7

The object compound [Ig] or its salt can be prepared by reducing the compound [If] or its salt.

This reaction may be carried out in substantially the same manner as Process 3, and therefore the reaction mode and reaction conditions [e.g. reducing agent, solvent, reaction temperature, etc.] of this reaction are to be referred to those as explained in Process 3.

PROCESS 8

The object compound [Ic] or its salt can be prepared by subjecting the compound [Ih] or its salt to hydrolysis. This reaction can be usually carried out in the presence of an acid.

Suitable acid may be an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.).

This reaction is preferably carried out in the presence of a trapping agent of aldehyde which is formed during the course of the reaction. Suitable trapping agent may be the compounds of the formula: $NH_2$-$R^{15}$ [VIII] wherein $R^{15}$ is hydroxy, lower alkoxy or amino, or salts thereof.

Suitable salts of the compound [VIII] may be an acid addition salt as described above.

This reaction is usually carried out in a conventional solvent such as water, methanol, ethanol, propanol, tetralin, tetrahydrofuran, acetonitrile, dioxane, chloroform, toluene, dimethylformamide, dimethylsulfoxide or any other solvent which does not adversely influence the reaction, or a mixture thereof.

The reaction temperature is not critical, and the reaction is usually carried out at ambient temperature or under cooling or warming or heating.

In the present reaction, in case that the compound wherein Y is CO is used as a starting compound, said CO may be converted to C═N—OH during the reaction, which is also included within the scope of the reaction.

PROCESS 9

The object compound [Ii] or its salt can be prepared by reacting the compound [Ic] or its salt with the compound [VI] or its salt.

This reaction is usually carried out in a conventional solvent such as water, methanol, ethanol, propanol, tetralin, tetrahydrofuran, dioxane, chloroform, dichloromethane, toluene, dimethylformamide, dimethylsulfoxide or any other organic solvent which does not adversely influence the reaction.

The reaction temperature is not critical, and the reaction is usually carried out at ambient temperature or under warming to heating.

PROCESS 10

The object compound [Ij] or its salt can be prepared by subjecting the compound [Ii] or its salt to reduction. The reduction may be carried out in substantially the same manner as Process 3, and therefor the reaction mode and reaction conditions [e.g. reducing agent, solvent, reaction temperature, etc.] of this reaction are to be referred to those as explained in Process 3.

PROCESS 11

The object compound [Ik] or its salt can be prepared by reacting the compound [Ia] or its salt with he compound [VII] or its salt.

This reaction is usually carried out in a conventional solvent such as water, methanol, ethanol, propanol, tetralin, tetrahydrofuran, dioxane, chloroform, toluene, dimethylformamide, dimethylsulfoxide or any other organic solvent which does not adversely influence the reaction.

The reaction temperature is not critical, and the reaction is usually carried out at ambient temperature or under warming to heating.

The compounds thus obtained by Processes 1 to 11 may be converted into aforesaid pharmaceutically acceptable salts thereof according to a conventional manner.

The new N-containing fused heterocyclic compounds [I] and pharmaceutical acceptable salts thereof possess antithrombotic activity, antiinflammatory activity, antiallergic activity and analgesic activity, and are useful for a therapeutic treatment of thrombosis [e.g. cerebral thrombosis, etc.], inflammation [e.g, edema, etc.], and allergic disease [e.g. asthma, etc.], and are useful as analgesic.

For the purpose of showing pharmaceutical activity of the N-containing fused heterocyclic compounds [I], pharmacological test data of the representative compounds of the N-containing fused heterocyclic compounds [I] are illustrated in the following.

PLATELET AGGREGATION IN VITRO

1. Test method

Platelet rich plasma (PRP) which contains 6–7×$10^8$ platelets/ml was prepared from rabbit blood. To the 200 μl of PRP, 5 μl of calcium chloride (1 mM) and 50 μl of 25 mM Tris-acetate solution (pH 7.4) containing 120 mM NaCl or test compound were added successively, and then stirred for 2 min. at 37° C. To the solution, 5 μl of adenosine diphosphate (ADP) (2.5 μM) or collagen (2.5 μg/ml) was added as an aggregation inducer. Aggregation was measured by using an aggregometer. (NKK HEMA-TRACER 1). Activities of inhibitors (test compounds) were expressed as $ID_{50}$ values i.e. Doses required to inhibit the platelet aggregation responses by 50%.

2. Test result

| Test compound | $ID_{50}$ (M) ADP | $ID_{50}$ (M) Collagen |
|---|---|---|
| Example 5 | $1.4 \times 10^{-5}$ | $1.4 \times 10^{-5}$ |
| Aspirin | $3.2 \times 10^{-3}$ | $3.1 \times 10^{-5}$ |

PLATELET AGGREGATION EX VIVO

1. Test method

Male Sprague-Dawley rats weighing about 250 g were used after overnight fasting. One hour after oral administration of test compound or vehicle of test compound (control), blood was collected into a tube containing 0.1 vol. of 3.8% sodium citrate. To the 0.45 ml of blood, 0.05 ml of collagen (final concentration 5.0 μg/ml) was added and then incubated for 5 min. at 37° C. under shaking.

The reaction was terminated by addition of 1 ml of 10 mM phosphate buffered saline (pH 7.4) containing 11.5 mM EDTA and 1% formalin. The reaction mixture was centrifuged at 70×g for 5 min. and platelet count of upper phase was measured by Technicon Auto Analizer.

Platelet aggregation was calculated according to the following formula:

$$\text{Platelet aggregation (\%)} = \frac{A - B}{A} \times 100$$

A. Platelet count after addition of vehicle of collagen

B. Platelet count after addition of collagen

Inhibition of the test compound was calculated according to the following formula;

$$\text{Inhibition (\%)} = \frac{C - D}{C} \times 100$$

C. Platelet aggregation (%) of control

D. Platelet aggregation (%) of Test compound

2. Test result

| Test compound | Dose (mg/kg) | Inhibition (%) |
|---|---|---|
| Example 5 | 10 | 2 |
| | 32 | 67 |
| | 100 | 100 |

CARRAGEENIN FOOD EDEMA

1. Test method

Male Sprague-Dawley rats weighing about 180 g were used in groups of five.

Paw edema was induced by subplantar injection of 1% carrageenin (0.1 ml/rat) into the right hind paw in carrageenin foot edema. The test compound was suspended in methylcellulose and administered orally 60 minutes before phlogogen.

Paw volume was measured with plethysmometer (Ugo Basil Co., Ltd.) by water displacement immersing the paw to the lateral malleolus. The difference of paw volume before and 3 hours after the phlogogen was designated as edema volume.

The data analyzed statistically by student's t-test.

2. Test result

| Test compound | Dose (mg/kg) | Inhibition (%) |
|---|---|---|
| Example 5 | 320 | 40.0* |

(note)
*$P < 0.05$
P: probability

SYSTEMIC ANAPHYLAXIS

1. Test method

Male Hartley guinea pigs (300–400 g, n=5) were passively sensitized with i.v. injection of rabbit anti-ovalbumin serum. 24 Hours later, test compound was administered orally. 30 Min. after administration of test compound, sensitized animals were placed for 2 min. in a chamber filled with antigen aerosol (ovalbumin) by a conventional nebulizer. Survived animals were regarded as being protected from systemic anaphylaxis.

2. Test result

| Test compound | Dose (mg/kg) | Survival (%) |
|---|---|---|
| Example 5 | 10 | 20 |
| | 100 | 100 |

ACETIC ACID-INDUCED WRITHING SYNDROME

1. Test method

Male Scl:ddy strain mice aged 6 weeks were used in groups of 10. The test compound was suspended in methylcellulose and administered orally. After 60 min., 20 ml/kg of 0.6% acetic acid solution was administered i.p. and writhing episodes between 3 and 13 min. after acetic acid injection were counted. The data was analyzed statistically by student's t-test.

2. Test result

| Test compound | Dose (mg/kg) | Inhibition (%) |
|---|---|---|
| Example 5 | 32 | 32.8* |

(note)
*$P < 0.01$
P: probability

For therapeutic administration, the object compounds [I] of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion.

If needed, there may be included in the above preparation auxiliary substance such as stabilizing agent, wetting or emulsifying agent, buffer or any other commonly used additives.

The effective ingredient may usually be administered with a unit dose of 0.01 mg/kg to 500 mg/kg, 1 to 4 times a day. However, the above dosage may be increased or decreased according to age, weight and conditions of the patient or the administering method.

The following preparations and examples are given only for the purpose of illustrating the present invention in more detail.

PREPARATION 1

3-Amino-5-chloro-2-mercaptopyridine (18.8 g) was added to an ice-cooled solution of phosgene (30 g) in toluene (350 ml). 10% Aqueous solution of sodium hydroxide (300 ml) was added dropwise to the stirred mixtured for a period of 1 hour below 20° C. The final mixture was stirred for 1.5 hous at ambient temperature and then stirred for an additional 1 hour at 50° C. After cooling, the aqueous layer was adjusted to pH 4.0 with 4N hydrochloric acid. The precipitates were collected by filtration, washed with water and dried over phosphorus pentoxide to give white powder of 6-chloro-2-oxo-1,2-dihydrothiazolo[5,4-b]pyridine (15.08 g).

IR (Nujol): 3150, 3100, 3000, 1660, 1590, 1210, 1120, 900 $cm^{-1}$.

NMR (DMSO-$d_6$, δ): 7.50 (1H, d, J=2 Hz), 8.27 (1H, d, J=2 Hz).

PREPARATION 2

Methyl chloroacetate (9.6 g) and potassium carbonate (11.1 g) were added to a solution of 6-chloro-2-oxo-1,2-dihydrothiazolo[5.4-b]pyridine (15.0 g ) in dry N,N-dimethylformamide (50 ml). The mixture was stirred for 30 minutes at 80° C. and then poured into cold water. The precipitates were collected by filtration, washed with water and dried over phosphorus pentoxide to give white powder of 6-chloro-1-methoxycarbonylmethyl-2-oxo-1,2-dihydrothiazolo[5,4-b]pyridine (20.52 g).

IR (Nujol): 1740, 1690, 1590, 1310, 1230, 1180, 960, 900, 880, 710 $cm^{-1}$.

NMR ($CDCl_3$, δ): 3.70 (3H, s), 4.65 (2H, s), 7.15 (1H, d, J=2 Hz), 8.23 (1H, d, J=2 Hz).

PREPARATION 3

An aqueous solution (30 ml) of potassium hydroxide (3.1 g) was added dropwise to an ice-cooled solution of 6-chloro-1-methoxycarbonylmethyl-2-oxo-1,2-dihydrothiazolo[5,4-b]pyridine (7.2 g) in tetrahydrofuran (70 ml). The mixture was stirred for 1 hour at ambient temperature and then adjusted to pH 3.0 with 2N hydrochloric acid. After evaporation of tetrahydrofuran, the residue was extracted with ethyl acetate (40 ml×5). The extracts were combined, dried over magnesium sulfate and concentrated under reduced pressure to give a crystalline product, which was recrystallized from ethyl acetate (200 ml) to affored 6-chloro-1-carboxymethyl-2-oxo-1,2-dihydrothiazolo[5,4-b]pyridine (4.93 g ) as crystals.

mp: 243°-246° C.

IR (Nujol): 3450, 1725, 1690, 1590, 1430, 1310, 1220, 880, 720, 690 $cm^{-1}$.

NMR (DMSO-$d_6$, δ): 4.83 (2H, s), 8.19 (1H, d, J=2 Hz), 8.39 (1H, d, J=2 Hz).

EXAMPLE 1

To an ice-cooled solution of a mixture of 6-chloro-1-carboxymethyl-2-oxo-1,2-dihydrothiazolo[5,4-b]pyridine (3.47 g) and N-hydroxysuccinimide (1.96 g) in N,N-dimethylformamide (20 ml) was gradually added N,N-dicyclohexylcarbodiimide (3.51 g). The mixture was stirred for 1 hour at ambient temperature and dicyclohexylurea that precipitated from the reaction mixture was removed by filtration. To a solution of piperazine (6.11 g) in N,N-dimethylformamide (80 ml) was added dropwise the filtrate for a period of 1.5 hours below 20° c. The final mixture was stirred for 4 hours at ambient temperature, and then filtered. The filtrate was concentrated under reduced pressure below 50° C. and the residue was dissolved in 2N hydrochloric acid. The aqueous solution was washed with chloroform and then adjusted to pH 9 with an aqueous solution of sodium hydrogen carbonate. The turbid solution was extracted with chloroform, and the extract was dried over magnesium sulfate and concentrated under reduced pressure to give a white powder of 6-choro-2-oxo-1-[(1-piperazinyl)carbonylmethyl]-1,2-dihydrothiazolo[5,4-b]pyridine (3.24 g).

mp: 169°-173° C.

IR (Nujol): 3300, 1710, 1640, 1580, 1420, 1310, 1250, 1190, 1120, 1040, 910, 880, 830, 790 $cm^{-1}$.

NMR ($CDCl_3$, δ): 1.6-2.1 (1H, broad s), 2.8-3.2 (4H, m), 3.5-3.8 (4H, m), 4.75 (2H, s), 7.32 (1H, d, J=2 Hz), 8.28 (1H, d, J=2 Hz).

EXAMPLE 2

To an ice-cooled solution of 2-oxo-3-benzothiazolineacetic acid [J. Prakt. Chem. 27 (3-4), 220-4 (1965); 8.1 g] and N-hydroxysuccinimide (5.4 g) in N,N-dimethylformamide (50 ml) was gradually added N,N-dicyclohexylcarbodiimide (9.6 g), and the mixture was stirred for an hour at ambient temperature. The dicyclohexylurea that precipitated from the reaction mixture was filtered off. To a stirred solution of piperazine (16.7 g) in N,N-dimethylformamide (200 ml) was added dropwise the filtrate for a period of 40 minutes below 20° C. The final mixture was stirred for 3.5 hours at ambient temperature and then filtered. The filtrate was concentrated under reduced pressure. The residue was dissolved in 2N hydrochloric acid and the solution was washed with chloroform. The aqueous layer was adjusted to pH 9 with an aqueous solution of sodium hydrogen carbonate, and the turbid solution was extracted with chloroform (80 ml×3). The extracts were combined and dried over magnesium sulfate. After evaporation of the solvent, 3-[(1-piperazinyl)carbonylmethyl]-2-benzothiazolinone (9.50 g) was obtained as white powders.

mp: 197°-201° C.

IR (Nujol): 3350, 1675, 1655, 1590, 1240, 755 $cm^{-1}$.

NMR ($DMSO-d_6$, δ): 1.0-2.0 (1H, broad s), 2.5-3.1 (4H, m), 3.1-3.6 (4H, m), 4.85 (2H, s), 7.0-7.7 (4H, m).

EXAMPLE 3

To a solution of 6-chloro-2-oxo-1-[(1-piperazinyl)carbonylmethyl]-1,2-dihydrothiazolo[5,4-b]pyridine (1.40 g) in chloroform (15 ml) was added isoamyl nitrite (3.0 ml) and the mixture was stirred for 11 hours at room temperature. Precipitated crystals were collected by filtration, washed with chloroform and dried to give colorless crystals of 6-chloro-2-oxo-1-[(4-nitroso-1-piperazinyl)carbonylmethyl]-1,2-dihydrothiazolo[5,4-b]pyridine (1.33 g).

mp: 220°-223° C. (dec.).

IR (Nujol): 1705, 1645, 1580, 1520, 990 $cm^{-1}$.

NMR ($DMSO-d_6$, δ): 3.5-4.0 (6H, m), 4.35 (2H, m), 5.04 (2H, s), 7.93 (1H, d, J=2 Hz), 8.30 (1H, d, J=2 Hz).

MASS: 341($M^+$), 311, 227 (Base), 199, 171.

EXAMPLE 4

To a solution of 3-[(1-piperazinyl)carbonylmethyl]-2-benzothiazolinone (3.0 g) in chloroform (50 ml) was added dropwise isoamyl nitrite (7.3 ml), for a period of 10 minutes below 20° C. The mixture was stirred for 18 hours at ambient temperature. Then, the reaction mixture was extracted with chloroform. The extract was washed with water, dried over magnesium sulfate and evaporated to give a crystalline product, which was recrystallized from a mixture of ethyl acetate and ethanol to give 3-[4-nitroso-1-piperazinyl)carbonylmethyl]-2-benzothiazolinone (2.54 g) as needles.

mp: 201°-203° C.

IR (Nujol): 1680, 1640, 1590, 1480, 1430, 1340, 1290, 1260, 1230, 1195, 1155, 985, 795, 750 $cm^{-1}$.

NMR ($DMSO-d_6$, δ): 3.4-4.0 (6H, m), 4.1-4.6 (2H, m), 5.00 (2H, s), 7.0-7.8 (4H, m).

EXAMPLE 5

5-Chloro-3-[(4-nitroso-1-piperazinyl)carbonylmethyl]-2-benzothiazolinone (9.2 g) was dissolved in a mixture of water (120 ml) and acetic acid (400 ml). To the solution stirred at room temperature zinc dust (12.0 g) was added over 3 hours. The mixture was stirred for additional 2 hours at room temperature. The zinc dust unused in the reaction was filtered and washed once with acetic acid. The filtrate and the washing were combined and evaporated to dryness. Chloroform (200 ml) was added to the residue and insoluble material was then filtered. The chloroform solution was concentrated to give a syrup which was subjected to a silica gel column chromatography using a mixture of chloroform and methanol (10:1). The desired fractions were combined and evaporated to give a pale yellow oil which was converted into hydrochloride using hydrogen chloride in absolute ether. The crude crystals obtained were recrystallized from aqueous ethanol to give 5-chloro-3-[(4-amino-1-piperazinyl)carbonylmethyl]-2-benzothiazolinone hydrochloride (4.03 g).

mp: 261°-263° C.

IR (Nujol): 2740, 2650, 2570, 2070, 1670, 1640, 1590, 1535, 1465, 1350, 1250, 1100, 805 $cm^{-1}$.

NMR ($D_2O$, δ): 3.0-3.3 (4H, m), 3.6-4.0 (4H, m), 4.93 (2H, s), 7.0-7.6 (3H, m).

Elemental analysis Calcd. for $C_{13}H_{15}ClN_4O_2S.HCl$: C, 42.98; H, 4.44; N, 15.42. Found: C, 43.14; H, 4.68; N, 15.54.

EXAMPLE 6

To a solution of 6-chloro-2-oxo-1-[(4-nitroso-1-piperazinyl)carbonylmethyl]-1,2-dihydrothiazolo[5,4-b]pyridine (1.42 g) in a mixture of acetic acid (30 ml) and water (9 ml) was added zinc dust (1.9 g) over 30 minutes with stirring at room temperature. The mixture was stirred for additional 2.5 hours at room temperature, then insoluble material was filtered and washed with acetic acid. The filtrate and the washings were combined and concentrated. The residue was subjected to column chromatography on silica gel (60 g) and eluted with a mixture of chloroform and methanol (10:1). The fractions containing the object compound were combined and concentrated. The crystalline residue (0.91 g) thus obtained was dissolved in ethanol (20 ml) and then a mixture of ethanol and hydrochloric acid solution was added thereto. The mixture was concentrated and the crystals (1.0 g) obtained were recrystallized from methanol (50 ml) to give colorless crystals of 6-chloro-2-oxo-1-[(4-amino-1-piperazinyl)carbonylmethyl]-1,2-dihydrothiazolo[5,4-b]pyridine hydrochloride (0.71 g).

mp: 238°-246° C. (dec.).

IR (Nujol): 2700, 2600, 1690, 1640, 1580, 1535, 1410, 1260, 1200 $cm^{-1}$.

NMR ($DMSO-d_6$, δ): 3.04 (4H, m), 3.63 (4H, broad s), 5.07 (2H, s), 8.02 (1H, d, J=2 Hz), 8.38 (1H, d, J=2 Hz), 9.90 (3H, broad s).

MASS: 327 ($M^+$), 227, 199, 171, 71 (Base).

Elemental analysis Calcd. for $C_{12}H_{14}ClN_5O_2S.HCl$: C, 39.57; H, 4.15; N, 19.23. Found: C, 39.82; H, 4.02; N, 19.38.

EXAMPLE 7

3-[(4-Nitroso-1-piperazinyl)carbonylmethyl]-2-benzothiazolinone (2.37 g) was dissolved in a mixture of acetic acid (30 ml) and water (9 ml). Zinc powder (3.54 g) was gradually added to the solution and the mixture was stirred for 1 hour at ambient temperature. After cooling, insoluble materials were filtered off and washed with acetic acid. The filtrate and washings were combined and concentrated under reduced pressure. The residue was dissolved in ethanol (200 ml) and an ethanolic solution of hydrogen chloride was added to the solution. The precipitates were filtered and recrystallized from a mixture of methanol (60 ml) and water (20 ml) to give white powders of 3-[(4-amino-1-piperazinyl)carbonylmethyl]-2-benzothiazolinone hydrochloride (1.58 g).

mp: 249°-258° C. (dec.)

IR (Nujol): 2750, 2700, 2620, 2080, 1670, 1640, 1610, 1545, 1250, 760 $cm^{-1}$.

NMR ($DMSO-d_6$, δ): 2.8-3.3 (4H, m), 3.3-3.9 (4H, m), 4.95 (2H, s), 7.0-7.5 (3H, m), 7.63 (1H, dd, J=2 and 7.5 Hz), 9.0-10.5 (3H, broad s).

Elemental analysis Calcd. for $C_{13}H_{16}N_4O_2S.HCl$: C, 47.49; H, 5.21; N, 17.04. Found: C, 47.54; H, 5.02; N, 17.14.

EXAMPLE 8

A suspension of 5-chloro-3-[(4-amino-1-piperazinyl)-carbonylmethyl]-2-benzothiazolinone hydrochloride (0.70 g) in anhydrous pyridine (15 ml) was stirred for 1 hour at room temperature and anhydrous acetic acid (0.5 ml) was added thereto and stirred for additional 3 hours at rom temperature. To the reaction mixture was added ice water and the resultant mixture was stirred for 10 minutes, then extracted with chloroform. The chloroform layer was washed with water, dried and then concentrated. Crystalline residue (0.58 g) obtained was recrystallized from chloroform-methanol (2:1 V/V, 30 ml) to give colorless crystals of 5-chloro-3-[(4-acetamido-1-piperazinyl)carbonylmethyl]-2-benzothiazolinone (0.25 g).

mp: 284°-285° C.

IR (Nujol): 3220, 1680, 1650 $cm^{-1}$.

NMR (DMSO-$d_6$, δ): 1.73, 1.98 (3H, 2s), 2.6-3.0 (4H, m), 3.3-3.7 (4H, m), 4.96 (2H, s), 7.26 (1H, dd, J=2 and 8 Hz), 7.45 (1H, d, J=2 Hz), 7.70 (1H, d, J=8 Hz), 8.50, 9.00 (1H, 2s).

MASS: 368 (M+), 170, 43 (Base).

Elemental analysis

Calcd. for $C_{15}H_{17}ClN_4O_3S$: C, 48.85; H, 4.65; N, 15.19. Found: C, 49.00; H, 4.57; N, 15.19.

EXAMPLE 9

Anhydrous acetic acid (2.08 ml) and formic acid (0.83 ml) were mixed and reacted for 30 minutes at room temperature. To the above reaction mixture was added 5-chloro-3-[(4-amino-1-piperazinyl)carbonylmethyl]-2-benzothiazolinone (1.5 g) and stirred for 2 hours at room temperature. White crystals were filtered, washed with ethyl acetate and recrystallized from a mixture of chloform and methanol to give colorless crystals of 5-chloro-3-[(4-formamido-1-piperazinyl)carbonylmethyl]-2-benzothiazlinone (1.14 g).

mp: 256°-258° C.

IR (Nujol): 3500, 3250, 1710, 1680, 1650, 1595, 1460 $cm^{-1}$.

NMR (DMSO-$d_6$, δ): 2.6-2.9 (4H, m), 3.3-3.7 (4H, m), 4.95 (2H, s), 7.1-7.8 (3H, m), 8.18 (1H, d, J=10 Hz), 9.07 (1H, d, J=1 Hz).

MASS: 354 (M+), 315, 198, 170, 84 (Base).

Elemental analysis Calcd. for $C_{14}H_{15}N_4ClO_3S$.-$\frac{2}{3}$MeOH: C, 46.83; H, 4.73; N, 14.89. Found: C, 46.50; H, 4.49; N, 15.19.

EXAMPLE 10

To a solution of 5-chloro-3-[(4-amino-1-piperazinyl)-carbonylmethyl]-2-benzothiazolinone (1.64 g) in methylene chloride (60 ml) were added potassium carbonate (860 mg) and mesyl chloride (0.96 ml) and stirred for 8 hours with reflux. Insoluble material was filtered off and the filtrate was evaporated and then recrystallized from a mixture of chloroform and methanol to give colorless crystals of 5-chloro-3-[(4-mesylamino-1-piperazinyl)carbonylmethyl]-2-benzothiazlinone (1.2 g).

mp: 202°-203° C.

IR (Nujol): 3230, 1680, 1655, 1595, 1460 $cm^{-1}$.

NMR (DMSO-$d_6$, δ): 2.7-3.0 (4H, m), 2.97 (3H, s) 3.3-3.8 (4H, m), 4.96 (2H, s), 7.22 (1H, dd, J=8, 2 Hz), 7.43 (1H, d, J=2 Hz), 7.68 (1H, d, J=8 Hz), 8.42 (1H, s). MASS: 403 (M+−1), 389, 324, 198, 170, 99 (Base)

Elemental analysis Calcd. for $C_{14}H_{17}ClN_4O_4S_2$: C, 41.53; H, 4.23; N, 13.84. Found: C, 41.07; H, 4.05; N, 13.84.

EXAMPLE 11

A mixture of 5-chloro-3-[(4-amino-1-piperazinyl)carbonylmethyl]-2-benzothiazolinone (0.85 g), anhydrous potassium carbonate (430 mg), dichloromethane (40 ml), dioxane (10 ml) and ethyl chloroformate (339 mg) was stirred for 1.5 hours at room temperature. The insoluble materials were filtered off and the filtrate was concentrated under reduced pressure. The residue was recrystallized from a mixture of chloroform and dioxane to give colorless crystals of 5-chloro-3-[(4-ethoxycarbonylamino-1-piperazinyl)carbonylmethyl]-2-benzothiazolinone (0.35 g).

mp: 160°-163° C. (dec.).

IR (Nujol): 3240, 1710, 1665, 1590, 1550, 1460 $cm^{-1}$.

NMR (DMSO-$d_6$, δ): 1.16 (3H, t, J=7 Hz), 2.6-3.0 (4H, m), 3.4-3.7 (4H, m), 4.02 (2H, q, J=7 Hz), 4.97 (2H, s), 7.1-7.8 (3H, m), 8.38 (1H, s). MASS: 398 (M+), 352, 310, 226, 198 (Base), 170.

Elemental analysis Calcd. for $C_{16}H_{19}N_4ClO_4S.\frac{1}{4}C_4H_8O_2$: C, 48.51; H, 5.03; N, 13.31. Found: C, 48.55; H, 5.02; N, 13.22.

EXAMPLE 12

A solution of 4-fluorobenzoyl chloride (761 mg) in dioxane (3 ml) was added dropwise to a mixture of 5-chloro-3-[(4-amino-1-piperazinyl)carbonylmethyl]-2-benzothiazolinone hydrochloride (872 mg), 1N-NaOH (5.3 ml), dioxane (30 ml) and water (5 ml) at 5° C. The resulting mixture was stirred for 30 minutes and concentrated under reduced pressure. The residue obtained was filtered, washed with water and ethyl acetate, and recrystallized from methanol to give 5-chloro-3-{[4-(4-fluorobenzamido)-1-piperazinyl]carbonylmethyl}-2-benzothiazolinone (0.61 g).

IR (Nujol): 3220, 1710, 1665, 1640, 1600, 1510, 1460 $cm^{-1}$.

NMR ($CF_3CO_2H$, δ): 4.0-4.6 (8H, m), 5.18 (2H, s), 7.1-7.6 (5H, m), 7.9-8.2 (2H, m).

Elemental analysis Calcd. for $C_{20}H_{18}ClFN_4O_3S$: C, 53.51; H, 4.04; N, 12.48. Found: C, 53.87; H, 4.18; N, 12.52.

EXAMPLE 13

A solution of 4-fluorophenyl isocyanate (273 mg) in dioxane (5 ml) was added dropwise to a mixture of 5-chloro-3-[(4-amino-1-piperazinyl)carbonylmethyl]-2-benzothiazolinone hydrochloride (981 mg), triethylamine (273 mg), dioxane (40 ml) and water (2 ml) at room temperature. The resulting mixture was stirred for 2 hours and concentrated under reduced pressure. The residue was filtered, washed with water and ethyl acetate, and recrystallized from N,N-dimethylformamide to give 5-chloro-3-{[4-[N'-(4-fluorophenyl)ureido]-1-piperazinyl]carbonylmethyl}-2-benzothiazolinone (0.82 g).

mp: >250° C.

IR (Nujol): 3650, 3430, 3300, 1680, 1660, 1590, 1530, 1510, 1460 $cm^{-1}$.

NMR ($CF_3CO_2H$, δ): 3.8-4.6 (8H, m), 5.20 (2H, s) 6.9-7.6 (7H, m), 8.3 (1H, broad s).

MASS: 463 (M+), 326, 226, 198, 170, 111 (Base).

Elemental analysis Calcd. for $C_{20}H_{19}N_5ClFO_3S$: C, 51.82; H, 4.13; N, 15.10. Found: C, 51.12; H, 4.42; N, 14.78.

EXAMPLE 14

To a solution of 5-chloro-3-[(4-amino-1-piperazinyl)-carbonylmethyl]-2-benzothiazolinone (1.64 g) in acetonitrile (50 ml) were added 37% formaldehyde solution (4 ml) and sodium cyanoborohydride (1 g) and the mixture was stirred for 25 minutes at room temperature and further for 1 hour neutralizing with acetic acid and concentrated. To a residue was added saturated sodium carbonate solution and extracted with chloroform. After drying over anhydrous magnesium sulfate, the solution was concentrated under reduced pressure. The residue was subjected to a column chromatography on silica gel (42 g) and eluted with a mixture of chloroform-methanol (20:1). The fractions containing the object compound were combined and concentrated under reduced pressure. The residue was washed with ether and then acetic acid to give 5-chloro-3-[(4-dimethylamino-1-piperazinyl)carbonylmethyl]-2-benzothiazolinone (0.32 g), which was dissolved with heating in a mixture of chloroform (10 ml) and ethanol (5 ml). After cooling, to the mixture was added ethanol solution containing hydrogen chloride (about 23%). The residue obtained by concentration under reduced pressure was recrystallized from a mixture of ethanol (10 ml) and water (0.5 ml) to give colorless crystals of 5-chloro-3-[(4-dimethylamino-1-piperazinyl)carbonylmethyl]-2-benzothiazlinone hydrochloride (0.31 g).

mp: 192°-194° C.

IR (Nujol): 3550, 2380, 1680, 1630, 1490 $cm^{-1}$. NMR (DMSO-$d_6$, δ): 2.85 (6H, s), 2.8-3.2 (4H, m), 3.4-3.8 (4H, m), 4.96 (2H, s), 7.20 (1H, dd, J=8, 2 Hz), 7.43 (1H, d, J=2 Hz), 7.68 (1H, d, J=8 Hz).

MASS: 354 (M+, Base), 226, 198, 170, 128.

Elemental analysis Calcd. for $C_{15}H_{20}Cl_2N_4O_2S.H_2O$: C, 44.02; H, 5.41; N, 13.69. Found: C, 44.13; H, 5.17; N, 13.59.

EXAMPLE 15

A solution of 5-chloro-3-[(4-amino-1-piperazinyl)carbonylmethyl]-2-benzothiazolinone (5.0 g) and 37% formaldehyde solution (1.38 ml) in acetonitrile (150 ml) was stirred for 1.5 hours at room temperature. The reaction mixture was concentrated under reduced pressure. The residue was subjected to column chromatography on silica gel (50 g) eluting with a mixture of chloroform and methanol (50:1). The fractions containing the desired compound were combined and concentrated under reduced pressure. The residue was recrystallized from ethanol (200 ml) to give colorless crystals of 5-chloro-3-[(4-methyleneamino-1-piperazinyl)carbonylmethyl]-2-benzothiazolinone (5.1 g).

mp: 150°-152° C.

IR (Nujol): 1685, 1650, 1590, 1464 $cm^{-1}$.

NMR (DMSO-$d_6$, δ): 2.8-3.2 (4H, m), 3.5-3.8 (4H, m), 4.96 (2H, s), 6.28, 6.58 (2H, ABq, J=10 Hz), 7.1-7.8 (3H, m).

MASS: 338 (M+), 310, 226, 198, 170, 18 (Base).

Elemental analysis Calcd. for $C_{14}H_{15}N_4ClO_2S$: C, 49.63; H, 4.46; N, 16.54. Found: C, 49.77; H, 4.32; N, 16.57.

EXAMPLE 16

A mixture of 5-chloro-3-[(4-methyleneamino-1-piperazinyl)carbonylmethyl]-2-benzothiazolinone (5.09 g), sodium borohydride (284 mg), tetrahydrofuran (80 ml), and ethanol (70 ml) was stirred for 3 hours at room temperature. The reaction mixture was concentrated under reduced pressure and the residue obtained was purified by column chromatography on silica gel eluting with a mixture of chloroform and methanol (20:1). The fractions containing the desired compoundwere combined and concentrated under reduced pressure. The white residue was dissolved in chloroform (5 ml), and 20% solution of hydrogen chloride in ethanol (1 ml) was added to the above solution. The white precipitates were filtered and recrystallized from a mixture of ethanol (10 ml) and water (2 ml) to give colorless crystals of 5-chloro-3-[(4-methylamino-1-piperazinyl)carbonylmethyl]-2-benzothiazolinone hydrochloride (0.5 g).

mp: 248°-250° C.

IR (Nujol): 3400, 2650, 2500, 1710, 1670, 1595 $cm^{-1}$.

NMR (DMSO-$d_6$, δ): 2.69 (3H, s), 2.8-3.8 (8H, m), 4.96 (2H, s), 7.1-7.8 (3H, m), 10.8 (2H, broad s).

MASS: 340 (M+), 310, 225, 198 (Base), 170.

Elemental analysis Calcd. for $C_{14}H_{18}Cl_2N_4O_2S$: C, 44.57; H, 4.81; N, 14.85. Found: C, 44.32; H, 4.52; N, 14.84.

EXAMPLE 17

In a similar manner to that of Example 1, 2 or 23, there were obtained the following compounds.

(1) 5-Chloro-3-[(1-piperazinyl)carbonylmethyl]-2-benzoxazolinone mp: 161°-171° C.

IR (Nujol): 3300, 1785, 1650 $cm^{-1}$.

NMR (DMSO-$d_6$, δ): 1.0-2.0 (1H, br s), 2.5-3.0 (4H, m), 3.3-3.7 (4H, m), 7.15 (1H, dd, J=7.5 Hz and 2 Hz), 7.40 (1H, d, J=7.5 Hz), 7.45 (1H, d, J=2 Hz).

MASS (m/e): 295 (M+), 182, 113, 85, 56 (base).

(2) 4-Chloro-3-[(1-piperazinyl)carbonylmethyl]-2-benzothiazolinone mp: 165°-166.5° C.

IR (Nujol): 3350, 1670, 1650 $cm^{-1}$.

NMR ($CDCl_3$, δ): 1.70 (1H, br s), 2.8-3.1 (4H, m), 3.4-3.7 (4H, m), 5.20 (2H, s), 6.8-7.4 (3H, m).

(3) 6-Chloro-3-[(1-piperazinyl)carbonylmethyl]-2-benzothiazolinone mp: 166°-168° C.

IR (Nujol): 3340, 1690, 1650 $cm^{-1}$.

NMR ($CDCl_3$, δ): 1.75 (1H, br s), 2.7-3.1 (4H, m), 3.4-3.7 (4H, m), 4.65 (2H, s), 6.92 (1H, d, J=8 Hz), 7.22 (1H, dd, J=8 Hz and 2 Hz), 7.38 (1H, d, J=2 Hz).

(4) 7-Chloro-3-[(1-piperazinyl)carbonylmethyl]-2-benzothiazolinone mp: 169°-172° C.

IR (Nujol): 3320, 1680, 1650 $cm^{-1}$.

NMR ($CDCl_3$, δ): 1.65 (1H, br s), 2.75-3.00 (4H, m), 3.45-3.65 (4H, m), 4.96 (2H, s), 6.90 (1H, dd, J=2.5 Hz and 7.0 Hz), 7.08 (1H, dd, J=2.5 Hz and 7.0 Hz), 7.20 (1H, dd, J=7.0 Hz).

(5) 5-Methyl-3-[(1-piperazinyl)carbonylmethyl]-2-benzothiazolinone mp: 185°-188° C.

IR (Nujol): 3370, 1690, 1640 $cm^{-1}$.

NMR ($CDCl_3$, δ): 1.70 (1H, broad s), 2.7-3.1 (4H, m), 3.5-3.8 (4H, m), 4.67 (2H, s), 6.7-7.4 (3H, m).

(6) 5-Trifluoromethyl-3-[(1-piiperazinyl)carbonylmethyl]-2-benzothiazolinone mp: 162°-163° C.

IR (Nujol): 3320, 1690, 1650, 1120 $cm^{-1}$.

NMR ($CDCl_3$, δ): 1.73 (1H, br s), 2.8–3.1 (4H, m), 3.5–3.7 (4H, m), 4.80 (2H, s), 7.23 (1H, s), 7.42 (1H, d, J=8 Hz), 7.56 (1H, d, J=8 Hz).

(7) 5-Chloro-3-[(1-homopiperazinyl)carbonylmethyl]-2-benzothiazolinone
mp: 179°–180° C.
IR (Nujol): 1680, 1640 $cm^{-1}$.
NMR ($CDCl_3$, δ): 1.6–2.1 (3H, m), 2.7–3.2 (4H, m), 3.5–3.8 (4H, m), 4.70 (2H, s), 7.0–7.4 (3H, m).

(8) 5-Chloro-3-[(3-methyl-1-piperazinyl)carbonylmethyl]-2-benzothiazolinone
mp: 153°–155° C.
IR (Nujol): 1690, 1650 $cm^{-1}$.
NMR ($CDCl_3$, 60° C., δ): 1.07 (3H, d, J=6 Hz), 2.14–3.2 (5H, m), 3.7–4.3 (2H, m), 4.65 (2H, s), 7.00 (1H, s), 7.15 (1H, d, J=8 Hz), 7.25 (1H, d, J=8 Hz). (9) 5-Chloro-6-phenyl-3-[(1-piperazinyl)carbonylmethyl]-2-benzothiazolinone
mp: 150°–153° C.
IR (Nujol): 3300, 1685, 1645 $cm^{-1}$.
NMR ($CDCl_3$, δ): 1.73 (1H, s), 2.8–3.2 (4H, m), 3.5–3.8 (4H, m), 4.73 (2H, s), 7.13 (1H, s), 7.43 (6H, br s).

(10) 5-Chloro-6-bromo-3-[(1-piperazinyl)carbonylmethyl]-2-benzothiazolinone
mp: 186°–189° C.
IR (Nujol): 3340, 1690, 1645, 1580, 1470 $cm^{-1}$.
NMR (DMSO-$d_6$, δ): 2.5–3.0 (4H, m), 3.3–3.7 (4H, m), 4.90 (2H, s), 7.63 (1H, s), 8.13 (1H, s).

(11) 6-Chloro-1-[(4-benzylideneamino-1-piperazinyl)-carbonylmethyl]-2,3-indolinedione
mp: 241°–243° C.
IR (Nujol): 1755, 1735, 1665, 1620, 1375, 1255, 1130, 1100, 1000 $cm^{-1}$.

(12) 6-Chloro-3-[(4-benzylideneamino-1-piperazinyl)-carbonylmethyl]-2-iminobenzothiazoline
mp: 158°–160° C. (dec.).
IR (Nujol): 3350, 1625, 1575, 990, 800, 750 $cm^{-1}$.

EXAMPLE 18

In a similar manner to that of Example 3 or 4, there were obtained the following compounds.

(1) 5-Chloro-3-[(4-nitroso-1-piperazinyl)carbonylmethyl]-2-benzoxazolinone
mp: 212°–215° C. (dec.).
IR (Nujol): 1775, 1660 $cm^{-1}$.
NMR (DMSO-$d_6$, δ): 3.3–4.1 (6H, m), 4.2–4.7 (2H, m) 4.93 (2H, s), 7.13 (1H, dd, J=7.5 Hz and 2 Hz), 7.38 (1H, d, J=7.5 Hz), 7.45 (1H, d, J=2 Hz).

(2) 4-Chloro-3-[(4-nitroso-1-piperazinyl)carbonylmethyl]-2-benzothiazolinone
mp: 179°–180° C.
IR (Nujol): 1695, 1675 $cm^{-1}$.
NMR (DMSO-$d_6$, δ): 3.5–4.1 (6H, m), 4.2–4.6 (2H, m), 5.28 (2H, s), 7.15 (1H, dd, J=7.5 Hz), 7.38 (1H, dd, J=7.5 Hz, 2 Hz), 7.68 (1H, dd, J=7.5 Hz and 2 Hz).

(3) 6-Chloro-3-[(4-nitroso-1-piperazinyl)carbonylmethyl]-2-benzothiazolinone
mp: 177°–179° C.
IR (Nujol): 1685, 1650 $cm^{-1}$.
NMR (DMSO-$d_6$, δ): 3.5–4.1 (6H, m), 4.2–4.6 (2H, m), 5.00 (2H, s), 7.2–7.5 (2H, m), 7.80 (1H, d, J=2.0 Hz).

(4) 7-Chloro-3-[(4-nitroso-1-piperazinyl)carbonylmethyl]-2-benzothiazolinone
mp: 227°–230° C. (dec.).
IR (Nujol): 1690, 1650 $cm^{-1}$.
NMR (DMSO-$d_6$, δ): 3.4–4.0 (6H, m), 4.1–4.5 (2H, m), 5.00 (2H, s), 7.1–7.5 (3H, m).

(5) 5-Methyl-3-[(4-nitroso-1-piperazinyl)carbonylmethyl]-2-benzothiazolinone
mp: 214°–217° C.
IR (Nujol): 1680, 1650 $cm^{-1}$.
NMR (DMSO-$d_6$, δ): 2.35 (3H, s), 3.5–4.1 (6H, m), 4.2–4.6 (2H, m), 4.97 (2H, s), 7.02 (1H, d, J=8 Hz), 7.07 (1H, s), 7.50 (1H, d, J=8 Hz).

(6) 5-Trifluoromethyl-3-[(4-nitroso-1-piperazinyl)carbonylmethyl]-2-benzothiazolinone
mp: 216°–218° C.
IR (Nujol): 1690, 1650 $cm^{-1}$.
NMR (DMSO-$d_6$, δ): 3.5–4.1 (6H, m), 4.3–4.7 (2H, m), 5.15 (2H, s), 7.60 (1H, d, J=8 Hz), 7.73 (1H, s), 8.00 (1H, d, J=8 Hz).

(7) 5-Chloro-3-[(4-nitroso-1-homopiperazinyl)carbonylmethyl]-2-benzothiazolinone
mp: 171°–172° C.
IR (Nujol): 1680, 1650 $cm^{-1}$.
NMR ($CDCl_3$, δ): 1.8–2.3 (2H, m), 3.4–4.1 (6H, m), 4.3–4.8 (4H, m), 6.9–7.5 (3H, m).

(8) 5-Chloro-3-[(3-methyl-4-nitroso-1-piperazinyl)carbonylmethyl]-2-benzothiazolinone
mp: 193°–194° C.
IR (Nujol): 1680, 1650 $cm^{-1}$.
NMR (DMSO-$d_6$, 60° C., δ): 1.07 and 1.47 (3H, 2d, J=7 Hz), 3.1–4.4 (5H, m), 4.4–4.9 (2H, m), 4.95 (2H, s), 7.15 (1H, dd, J=8 Hz and 2 Hz), 7.31 (1H, d, J=2 Hz), 7.59 (1H, d, J=8 Hz).

(9) 5-Chloro-6-phenyl-3-[(4-nitroso-1-piperazinyl)carbonylmethyl]-2-benzothiazolinone
mp: 263°–266° C.
IR (Nujol): 1680, 1660 $cm^{-1}$.

(10) 5-Chloro-6-bromo-3-[(4-nitroso-1-piperazinyl)carbonylmethyl]-2-benzothiazolinone
mp: >260° C.
IR (Nujol): 1680, 1590 $cm^{-1}$.

(11) 5-Chloro-3-[(4-nitroso-1-piperazinyl)carbonylmethyl]-2-benzothiazolinone
mp: 212°–214° C.
IR (Nujol): 1670, 1590 $cm^{-1}$.

EXAMPLE 19

In a similar manner to that of Example 5, 6 or 7 there were obtained the following compounds.

(1) 5-Chloro-3-[(4-amino-1-piperazinyl)carbonylmethyl]-2-benzoxazolinone hydrochloride
mp: 240°–242° C. (dec).
IR (Nujol): 2650, 2600, 1775, 1650, 1600, 1540, 1250, 1030, 935, 810, 690 $cm^{-1}$.
NMR (DMSO-$d_6$, δ): 2.8–3.2 (4H, m), 3.5–3.8 (4H, m), 4.90 (2H, s), 7.15 (1H, dd, J=9 Hz and 2 Hz), 7.38 (1H, d, J=9 Hz), 7.45 (1H, d, J=2 Hz), 9.4–10.4 (1H, broad s).
MASS (m/e): 310 ($M^+$), 182, 71 (base).
Analysis Calcd. for $C_{13}H_{15}ClN_4O_3.HCl$: C 44.97, H 4.64, N 16.14. Found: C 44.74, H 4.97, N 16.08.

(2) 4-Chloro-3-[(4-amino-1-piperazinyl)carbonylmethyl]-2-benzothiazolinone hydrochloride
mp: 237°–251° C. (dec.).
IR (Nujol): 2760, 2700, 2610, 1665, 1630 $cm^{-1}$.
NMR (DMSO-$d_6$, δ): 2.8–3.2 (4H, m), 3.5–3.9 (4H, m), 5.21 (2H, s), 7.18 (1H, d, J=7.5 Hz), 7.38 (1H, dd, J=7.5 Hz and 2.0 Hz), 7.70 (1H, dd, J=7.5 Hz and 2 Hz), 9.5–10.3 (3H, broad s).
MASS (m/e): 326 ($M^+$), 226, 198 (base), 170, 71.
Analysis Calcd. for $C_{13}H_{15}ClN_4O_2S.HCl$: C 42.98, H 4.44, N 15.42. Found: C 42.93, H 4.69, N 15.52.

(3) 6-Chloro-3-[(4-amino-1-piperazinyl)carbonylmethyl]-2-benzothiazolinone hydrochloride mp: 215°-243° C. (dec.).

IR (Nujol): 2700, 2600, 1670, 1650 $cm^{-1}$.

NMR (DMSO-$d_6$, δ): 2.9–3.3 (4H, m), 3.5–3.8 (4H, m), 4.99 (2H, s), 7.25 (1H, d, J=8 Hz), 7.42 (1H, dd, J=8 Hz and 2 Hz), 7.82 (1H, d, J=2 Hz), 9.2–10.5 (3H, br s).

MASS (m/e): 326 (M+), 198, 170, 71, 36 (base).

Analysis Calcd. for $C_{13}H_{15}ClN_4O_2S.HCl.\frac{1}{2}/H_2O$: C 41.94, H 4.60, N 14.05. Found: C 41.75, H 4.46, N 15.19.

(4) 7-Chloro-3-[(4-amino-1-piperazinyl)carbonylmethyl]-2-benzothiazolinone hydrochloride mp: 233°-242° C. (dec.).

IR (Nujol): 2750–2600, 1690, 1670 $cm^{-1}$.

NMR (DMSO-$d_6$, δ): 2.8–3.2 (4H, m), 3.4–3.8 (4H, m), 5.00 (2H, s), 7.1–7.5 (3H, m), 9.2–9.9 (3H, broad s).

MASS (m/e): 326 (M+, base).

Analysis Calcd. for $C_{13}H_{15}ClN_4O_2S.HCl$: C 42.98, H 4.44, N 15.42. Found: C 42.57, H 4.65, N 15.38.

(5) 5-Methyl-3-[(4-amino-1-piperazinyl)carbonylmethyl]-2-benzothiazolinone hydrochloride mp: 230°-240° C. (dec.).

IR (Nujol): 2750, 2670, 2610, 1670, 1645 $cm^{-1}$.

NMR (DMSO-$d_6$, δ): 2.34 (3H, s), 2.8–3.2 (4H, m), 3.4–3.8 (4H, m), 4.92 (2H, s), 7.00 (1H, d, J=7.5 Hz), 7.04 (1H, s), 7.49 (1H, d, J=7.5 Hz), 9.3–10.3 (3H, broad s).

MASS (m/e): 306 (M+), 206, 178, 150, 71 (base).

Analysis Calcd. for $C_{14}H_{18}N_4O_2S.HCl$: C 49.05, H 5.59, N 16.34. Found: C 49.13, H 5.61, N 16.46.

(6) 5-Trifluoromethyl-3-[(4-amino-1-piperazinyl)carbonylmethyl]-2-benzothiazolinone hydrochloride mp: 250°-260° C. (dec.).

IR (Nujol): 2750, 2670, 1690, 1655 $cm^{-1}$.

NMR (DMSO-$d_6$, δ): 2.8–3.2 (4H, m), 3.5–3.8 (4H, m), 5.07 (2H, s), 7.48 (1H, d, J=7.5 Hz), 7.60 (1H, s), 7.87 (1H, d, J=7.5 Hz), 9.3–9.9 (3H, broad s).

MASS (m/e): 360 (M+), 204, 71 (base).

Analysis Calcd. for $C_{14}H_{15}F_3N_4O_2S.HCl.\frac{1}{2}H_2O$: C 41.44, H 4.22, N 13.81. Found: C 41.51, H 4.45, N 13.81.

(7) 5-Chloro-3-[(4-amino-1-homopiperazinyl)carbonylmethyl]-2-benzothiazolinone hydrochloride mp: 228°-232° C.

IR (Nujol): 3280, 3160, 2570, 1710, 1660, 1620, 1590, 1180, 1080, 900, 800 $cm^{-1}$.

NMR (DMSO-$d_6$, δ): 1.8–2.3 (2H, m), 2.9–3.9 (8H, m), 4.95 (2H, s), 7.25 (1H, dd, J=8 Hz and 2 Hz), 7.48 (1H, d, J=2 Hz), 7.71 (1H, d, J=8 Hz), 8.8–10.5 (3H, broad s).

Analysis Calcd. for $C_{14}H_{17}ClN_4O_2S.HCl$: C 44.57, H 4.81, N 14.85. Found: C 44.91, H 4.87, N 14.92.

(8) 5-Chloro-3-[(4-amino-3-methyl-1-piperazinyl)carbonylmethyl]-2-benzothiazolinone hydrochloride mp: 168°-170° C.

IR (Nujol): 3400, 2670, 2600, 1680, 1655 $cm^{-1}$.

NMR (DMSO-$d_6$, 60° C., δ): 1.22 (3H, d, J=5 Hz), 2.7–3.6 (5H, m), 3.8–4.2 (2H, m), 4.94 (2H, s), 7.15 (1H, dd, J=8 Hz and 2 Hz), 7.33 (1H, d, J=2 Hz), 7.58 (1H, d, J=8 Hz), 8.0–10.0 (3H, broad s).

Analysis Calcd. for $C_{14}H_{17}ClN_4O_2S.HCl.H_2O$: C 42.54, H 5.10, N 14.17. Found: C 42.97, H 5.12, N 13.80.

(9) 5-Chloro-6-phenyl-3-[(4-amino-1-piperazinyl)carbonylmethyl]-2-benzothiazolinone hydrochloride mp: >270° C.

IR (Nujol): 2700, 2600, 1690, 1655, 1600, 1535, 1460, 1260, 1245, 1175, 1075, 990 $cm^{-1}$.

NMR (DMSO-$d_6$, δ): 2.9–3.3 (4H, m), 3.6–3.9 (4H, m), 5.07 (2H, s), 7.5–7.8 (7H, m), 9.8 (3H, br s).

(10) 5-Chloro-6-bromo-3-[(4-amino-1-piperazinyl)carbonylmethyl]-2-benzothiazolinone hydrochloride mp: 263°-265° C. (dec.).

IR (Nujol): 2650, 2600, 1705, 1660, 1590, 1520, 1470, 1380, 1350, 1310, 1240, 1190, 1070, 990 $cm^{-1}$.

NMR (DMSO-$d_6$, δ): 2.8–3.3 (4H, m), 3.5–3.9 (4H, m), 5.00 (2H, s), 7.70 (1H, s), 8.17 (1H, s), 9.7 (3H, br s).

(11) 6-Chloro-1-[(4-amino-1-piperazinyl)carbonylmethyl]-3-hydroxyimino-2-indolinone hydrochloride mp: 209°-214° C.

IR (Nujol): 2600, 1715, 1640, 1610, 1380, 1270, 1250, 1200, 1100, 1040, 1025 $cm^{-1}$.

NMR (DMSO-$d_6$, δ): 2.8–3.3 (4H, m), 3.4–3.8 (4H, m), 4.77 (2H, s), 7.13 (1H, d, J=8 Hz), 7.20 (1H, s), 7.97 (1H, d, J=8 Hz).

MASS (m/e): 337 (M+), 320 (base peak).

(12) 6-Chloro-3-[(4-amino-1-piperazinyl)carbonylmethyl]-2-iminobenzothiazoline mp: 137°-142° C. (dec.).

IR (Nujol): 3250, 1655, 1610, 1585, 1240, 1160, 1025, 960, 800 $cm^{-1}$.

NMR ($CDCl_3$, δ): 2.58 (4H, t, J=5 Hz), 3.64 (4H, t, J=5 Hz), 4.70 (2H, s), 6.75 (1H, d, J=8 Hz), 7.10 (1H, dd, J=2 Hz and 8 Hz), 7.15 (1H, d, J=2 Hz).

MASS (m/e): 325 (M+), 309 (base), 225.

(13) 6-Nitro-3-[(4-amino-1-piperazinyl)carbonylmethyl]-2-benzothiazolinone hydrochloride mp: 240°-242° C.

IR (Nujol): 2700, 2600, 1680, 1650, 1605, 1590, 1515, 1460, 1380, 1340, 1250, 1195, 895 $cm^{-1}$.

NMR (DMSO-$d_6$, δ): 2.9–3.9 (8H, m), 5.13 (2H, s), 7.50 (1H, d, J=9 Hz), 8.30 (1H, dd, J=9 Hz, 3 Hz), 8.77 (1H, d, J=3 Hz), 9.8 (3H, br s).

EXAMPLE 20

A mixture of 5-chloro-3-[(4-amino-1-piperazinyl)carbonylmethyl]-2-benzothiazolinone hydrochloride (2.6 g), N-(p-nitrobenzyloxycarbonyl)acetamidine (2.0 g) and dichloromethane (24 ml) in ethanol (50 ml) was refluxed for 3 hours. The mixture was concentrated under reduced pressure. The residue was subjected to column chromatography on silica gel (100 g) eluting with a mixture of chloroform and methanol (20:1). The fractions containing the desired compound were combined and evaporated to give pale yellow powders of 5-chloro-3-{[4-[N-(p-nitrobenzyloxycarbonyl)acetimidoylamino]-1-piperazinyl]carbonylmethyl}-2-benzothiazolinone (3.2 g).

IR (Film): 3300, 1750, 1695, 1680, 1660, 1630, 1590, 1520 $cm^{-1}$.

NMR (DMSO-$d_6$, δ): 2.1–2.9 (7H, m), 3.4–3.8 (4H, m), 4.95 (2H, s), 5.30 (2H, s), 7.1–7.8 (5H, m), 8.1–8.4 (3H, m).

EXAMPLE 21

A mixture of 5-chloro-3-{[4-[N-(p-nitrobenzyloxycarbonyl)acetimidoylamino]-1-piperazinyl]carbonylmethyl}-2-benzothiazolinone (2.0 g), acetic acid (0.3 ml), water (3 ml), 10% palladium on carbon (2.0 g) in tetrahydrofuran (40 ml) and methanol (20 ml) was incubated under an atmosphere of hydrogen for 3 hours. Palladium on carbon was filtered off, and the filtrate was coevaporated with ethanol. The residue obtained was purified by aluminum column chromatography, treated with hydrogen chloride in ethanol, and recrystallized from a mixture of water, ethanol and ether to give yellow crystals of 5-chloro-3-[(4-acetimidoylamino-1-piperazinyl)carbonylmethyl]-2-benzothiazolinone hydrochloride (0.3 g).

mp: 194°-200° C.
IR (Nujol): 3400, 1695, 1660, 1595, 1470 cm$^{-1}$.
NMR (DMSO-$d_6$, δ): 2.16 (3H, s), 2.6–3.1 (4H, m), 3.5–4.0 (4H, m), 5.01 (2H, s), 7.2–7.8 (3H, m), 8.77 (1H, s), 9.56 (1H, s), 11.52 (1H, s).
MASS (m/e): 368 (M+, base), 334, 198.
Analysis Calcd. for $C_{15}H_{19}N_5Cl_2O_2S \cdot \frac{2}{3}H_2O$: C 43.28, H 4.92, N 16.82. Found: C 43.18, H 5.26, N 16.58.

EXAMPLE 22

To a solution of 5-chloro-3-[(1-piperazinyl)carbonylmethyl]-2-benzothiazolinone (3.0 g) in a mixture of N,N-dimethylformamide (30 ml) and water (5 ml) was added S-methylisothiourea sulfate (4.0 g). The mixture was stirred for 8 hours at 80° C. and then cooled. The precipitates formed were filtered and recrystallized from water (100 ml) to give 5-chloro-3-[(4-amidino-1-piperazinyl)carbonylmethyl]-2-benzothiazolinone hemisulfate (2.63 g).

mp: 282°-285° C. (dec.).
IR (Nujol): 3350, 3070, 1705, 1660, 1610 cm$^{-1}$.
NMR (DMSO-$d_6$, δ): 3.3–4.0 (8H, m), 4.97 (2H, s), 7.19 (1H, dd, J=7.5 Hz and 2 Hz), 7.43 (1H, d, J=2 Hz), 7.62 (1H, d, J=7.5 Hz), 7.9–9.0 (4H, broad s).
Analysis Calcd. for $C_{14}H_{16}ClN_5O_2S \cdot \frac{1}{2}H_2SO_4$: C 41.74, H 4.25, N 17.38. Found: C 41.29, H 4.44, N 17.34.

EXAMPLE 23

(1) Piperazine (86.14 g, 1 mol) was dissolved in a cooled mixture of acetic acid (300 g) and water (430 ml). To this solution, was added dropwise a solution of sodium nitrite (69 g, 1 mol) dissolved in water (172 ml) at 10° C., and the reaction mixture was stirred for an hour at the same temperature. Then zinc powder (172.3 g) was added to the solution containing 1-nitrosopiperazine by portions below 40° C., and after addition, the reaction mixture was stirred for additional an hour and filtered. The cake of zinc was washed with water (172 ml), and benzaldehyde (106.1 g) dissolved in 424 ml of ethanol was added to the combined solution containing 1-aminopiperazine of the filtrate and washings. After stirring for an hour at room temperature, ethyl acetate (1034 ml) and ammonium chloride (281.4 g) was added to the mixture and the pH was adjusted to 9.50 with 6N sodium hydroxide solution. The insoluble materials in the organic layer was filtered off, and the aqueous layer was extracted again with ethyl acetate (690 ml). The combined extract containing 1-benzylideneaminopiperazine was dried over magnesium sulfate, and after filtration, magnesium sulfate was washed with 300 ml of methylene chloride and the washings were combined with the filtrate.

(2) To a suspension of 3-carboxymethyl-5-chloro-2-benzothiazolinone (121.84 g, 0.5 mol) in a mixed solvent of methylene chloride (610 ml) and dimethylformamide (61 ml), was added thionyl chloride (61 g), and the mixture was stirred under reflux for an hour. To the solution of 1-benzylideneaminopiperazine obtained by the reaction (1) was added triethylamine (126.5 g), and the above-mentioned solution of the acid chloride dropwise below 0° C. After addition, the reaction mixture was stirred for an hour at the same temperature. The mixture was concentrated to one third volume and methanol (1200 ml) was added. The precipitates were filtered, washed with methanol (1200 ml) and dried to give 5-chloro-3-[(4-benzylideneamino-1-piperazinyl)carbonylmethyl]-2-benzothiazolinone (189.0 g).

mp: 213°-215° C.
IR (Nujol): 1700 (sh), 1680, 1650, 1590 cm$^{-1}$.
NMR (DMSO-$d_6$, δ): 2.87–3.47 (4H, m), 3.47–3.93 (4H, m), 5.00 (2H, s), 7.10–7.87 (9H, m).

EXAMPLE 24

In a similar manner to that of Example 1, 2 or 23, there were obtained the following compounds.

(1) 5-Chloro-3-{[4-(2-hydroxybenzylideneamino)-1-piperazinyl]carbonylmethyl}-2-benzothiazolinone
mp: 206°-207° C.
IR (Nujol): 1690, 1660, 1590 cm$^{-1}$.
NMR (DMSO-$d_6$, δ): 3.0–3.5 (4H, m), 3.5–4.1 (4H, m), 5.00 (2H, s), 7.3–7.8 (8H, m), 11.07 (1H, s).

(2) 5-Chloro-3-[(4-isobutylideneamino-1-piperazinyl)carbonylmethyl]-2-benzothiazolinone
mp: 147°-149° C.
IR (Nujol): 1690, 1650, 1590 cm$^{-1}$.
NMR (CDCl$_3$, δ): 1.05 (6H, d, J=7 Hz), 2.45 (1H, sepl, J=7 Hz), 3.00 (4H, m), 3.73 (4H, m), 4.70 (2H, s), 6.87–7.43 (4H, m).

(3) 6-Nitro-3-[(4-benzylideneamino-1-piperazinyl)carbonylmethyl]-2-benzothiazolinone
mp: 248°-250° C.
IR (Nujol): 1690, 1660, 1460, 1340, 1250, 1140, 990 cm$^{-1}$.

(4) 6-Chloro-2-oxo-1-[(4-nitroso-1-piperazinyl)carbonylmethyl]-1,2-dihydrothiazolo[5,4-b]pyridine
mp: 220°-223° C. (dec.).
IR (Nujol): 1705, 1645, 1580, 1420, 990 cm$^{-1}$.
NMR (DMSO-$d_6$, δ): 3.5–4.0 (6H, m), 4.35 (2H, m), 5.04 (2H, s), 7.93 (1H, d, J=2 Hz), 8.30 (1H, d, J=2 Hz).
MASS: 341 (M+), 311, 227 (Base), 199, 171.

(5) 3-[(4-Nitroso-1-piperazinyl)carbonylmethyl]-2-benzothiazolinone
mp: 201°-203° C.
IR (Nujol): 1680, 1640, 1590, 1480, 1430, 1340, 1290, 1260, 1230, 1195, 1155, 985, 795, 750 cm$^{-1}$.
NMR (DMSO-$d_6$, δ): 3.4–4.0 (6H, m), 4.1–4.6 (2H, m), 5.00 (2H, s), 7.0–7.8 (4H, m).

(6) 5-Chloro-3-[(4-amino-1-piperazinyl)carbonylmethyl]-2-benzothiazolinone hydrochloride
mp: 261°-263° C.
IR (Nujol): 2740, 2650, 2570, 2070, 1670, 1640, 1590, 1535, 1465, 1350, 1250, 1100, 805 cm$^{-1}$.
NMR (D$_2$O, δ): 3.0–3.3 (4H, m), 3.6–4.0 (4H, m), 4.93 (2H, s), 7.0–7.6 (3H, m).
Elemental analysis Calcd. for $C_{13}H_{15}ClN_4O_2S \cdot HCl$: C 42.98, H 4.44, N 15.42. Found: C 43.14, H 4.68, N 15.54.

(7) 6-Chloro-2-oxo-1-[(4-amino-1-piperazinyl)carbonylmethyl]-1,2-dihydrothiazolo[5,4-b]pyridine hydrochloride
mp: 238°-246° C. (dec.).
IR (Nujol): 2700, 2600, 1690, 1640, 1580, 1535, 1410, 1260, 1200 cm$^{-1}$.
NMR (DMSO-$d_6$, δ): 3.04 (4H, m), 3.63 (4H, broad s), 5.07 (2H, s), 8.02 (1H, d, J=2 Hz), 8.38 (1H, d, J=2 Hz), 9.90 (3H, broad s).
MASS: 327 (M+), 227, 199, 171, 71 (Base).
Elemental analysis Calcd. for $C_{12}H_{14}ClN_5O_2S \cdot HCl$: C 39.57, H 4.15, N 19.23. Found: C 39.82, H 4.02, N 19.38.

(8) 3-[(4-Amino-1-piperazinyl)carbonylmethyl]-2-benzothiazolinone hydrochloride
mp: 249°-258° C. (dec.).

IR (Nujol): 2750, 2700, 2620, 2080, 1670, 1640, 1610, 1545, 1260, 760 $cm^{-1}$.

NMR (DMSO-$d_6$, δ): 2.8–3.3 (4H, m), 3.3–3.9 (4H, m), 4.95 (2H, s), 7.0–7.5 (3H, m), 7.63 (1H, dd, J=2 Hz and 7.5 Hz), 9.0–10.5 (3H, broad s).

Elemental analysis Calcd. for $C_{13}H_{16}N_4O_2S.HCl$: C 47.49, H 5.21, N 17.04. Found: C 47.54, H 5.02, N 17.14.

(9) 5-Chloro-3-[(4-acetamido-1-piperazinyl)carbonylmethyl]-2-benzothiazolinone mp: 284°-285° C.

IR (Nujol): 3220, 1680, 1650 $cm^{-1}$.

NMR (DMSO-$d_6$, δ): 1.73, 1.98 (3H, 2s), 2.6–3.0 (4H, m), 3.3–3.7 (4H, m), 4.96 (2H, s), 7.26 (1H, dd, J=2 Hz and 8 Hz), 7.45 (1H, d, J=2 Hz), 7.70 (1H, d, J=8 Hz), 8.50, 9.00 (1H, 2s).

MASS: 368 (M+), 170, 43 (Base).

Elemental analysis Calcd. for $C_{15}H_{17}ClN_4O_3S$: C 48.85, H 4.65, N 15.19. Found: C 49.00, H 4.57, N 15.19.

(10) 5-Chloro-3-[(4-formamido-1-piperazinyl)carbonylmethyl]-2-benzothiazolinone mp: 256°-258° C.

IR (Nujol): 3500, 3250, 1710, 1680, 1650, 1595, 1460 $cm^{-1}$.

NMR (DMSO-$d_6$, δ): 2.6–2.9 (4H, m), 3.3–3.7 (4H, m), 4.95 (2H, s), 7.1–7.8 (3H, m), 8.18 (1H, d, J=10 Hz), 9.07 (1H, d, J=10 Hz).

MASS: 354 (M+), 315, 198, 170, 84 (Base).

Elemental analysis Calcd. for $C_{14}H_{15}N_4OClO_3S$.-⅗MeOH: C 46.83, H 4.73, N 14.89. Found: C 46.50, H 4.49, N 15.19.

(11) 5-Chloro-3-[(4-mesylamino-1-piperazinyl)carbonylmethyl]-2-benzothiazolinone mp: 202°-203° C.

IR (Nujol): 3230, 1680, 1655, 1595, 1460 $cm^{-1}$.

NMR (DMSO-$d_6$, δ): 2.7–3.0 (4H, m), 2.97 (3H, s), 3.3–3.8 (4H, m), 4.96 (2H, s), 7.22 (1H, dd, J=8 Hz, 2 Hz), 7.43 (1H, d, J=2 Hz), 7.68 (1H, d, J=8 Hz), 8.42 (1H, s).

MASS: 403 (M+), 389, 324, 198, 170, 99 (Base).

Elemental analysis Calcd. for $C_{14}H_{17}ClN_4O_4S$: C 41.53, H 4.23, N 13.84. Found: C 41.07, H 4.05, N 13.84.

(12) 5-Chloro-3-[(4-ethoxycarbonylamino-1-piperazinyl)carbonylmethyl]-2-benzothiazolinone mp: 160°-163° C. (dec.).

IR (Nujol): 3240, 1710, 1665, 1590, 1550, 1460 $cm^{-1}$.

NMR (DMSO-$d_6$, δ): 1.16 (3H, t, J=7 Hz), 2.6–3.0 (4H, m), 3.4–3.7 (4H, m), 4.02 (2H, q, J=7 Hz), 4.97 (2H, s), 7.1–7.8 (3H, m), 8.38 (1H, s).

MASS: 398 (M+), 352, 310, 226, 198 (Base), 170.

Elemental analysis Calcd. for $C_{16}H_{19}N_4ClO_4S$.¼$C_4H_8O_2$: C 48.51, H 5.03, N 13.31. Found: C 48.55, H 5.02, N 13.22.

(13) 5-Chloro-3-{[4-(4-fluorobenzamido)-1-piperazinyl]carbonylmethyl}-2-benzothiazolinone IR (Nujol): 3220, 1710, 1665, 1640, 1600, 1510, 1460 $cm^{-1}$.

NMR ($CF_3CO_2H$, δ): 4.0–4.6 (8H, m), 5.18 (2H, s), 7.1–7.6 (5H, m), 7.9–8.2 (2H, m).

Elemental analysis Calcd. for $C_{20}H_{18}ClFN_4O_3S$: C 53.51, H 4.04, N 12.48. Found: C 53.87, H 4.18, N 12.52.

(14) 5-Chloro-3-{[4-[N'-(4-fluorophenyl)ureido]-1-piperazinyl]carbonylmethyl}-2-benzothiazolinone mp: >250° C.

IR (Nujol): 3650, 3430, 3300, 1680, 1660, 1590, 1530, 1510, 1460 $cm^{-1}$.

NMR ($CF_3CO_2H$, δ): 3.8–4.6 (8H, m), 5.20 (2H, s), 6.9–7.6 (7H, m), 8.3 (1H, broad s).

MASS: 463 (M+), 326, 226, 198, 170, 111 (Base).

Elemental analysis Calcd. for $C_{20}H_{19}N_5ClFO_3S$: C 51.82, H 4.13, N 15.10. Found: C 51.12, H 4.42, N 14.78.

(15) 5-Chloro-3-[(4-dimethylamino-1-piperazinyl)carbonylmethyl]-2-benzothiazolinone hydrochloride mp: 192°-194° C.

IR (Nujol): 3550, 2380, 1680, 1630, 1490 $cm^{-1}$.

NMR (DMSO-$d_6$, δ): 2.85 (6H, s), 2.8–3.2 (4H, m), 3.4–3.8 (4H, m), 4.96 (2H, s), 7.20 (1H, dd, J=8 Hz, 2 Hz), 7.43 (1H, d, J=2 Hz), 7.68 (1H, d, J=8 Hz).

MASS: 354 (M+, Base), 226, 198, 170, 128.

Elemental analysis Calcd. for $C_{15}H_{20}Cl_2N_4O_2S.H_2O$: C 44.02, H 5.41, N 13.69. Found: C 44.13, H 5.17, N 13.59.

(16) 5-Chloro-3-[(4-methyleneamino-1-piperazinyl)carbonylmethyl]-2-benzothiazolinone mp: 150°-152° C.

IR (Nujol): 1685, 1650, 1590, 1465 $cm^{-1}$.

NMR (DMSO-$d_6$, δ): 2.8–3.2 (4H, m), 3.5–3.8 (4H, m), 4.96 (2H, s), 6.28, 6.58 (2H, ABq, J=10 Hz), 7.1–7.8 (3H, m).

MASS: 338 (M+), 310, 226, 198, 170, 18 (Base).

Elemental analysis Calcd. for $C_{14}H_{15}N_4ClO_2S$: C 49.63, H 4.46, N 16.54. Found: C 49.77, H 4.32, N 16.57.

(17) 5-Chloro-3-[(4-methylamino-1-piperazinyl)carbonylmethyl]-2-benzothiazolinone hydrochloride mp: 248°-250° C.

IR (Nujol): 3400, 2650, 2500, 1710, 1670, 1595 $cm^{-1}$.

NMR (DMSO-$d_6$, δ): 2.69 (3H, s), 2.8–3.8 (8H, m), 4.96 (2H, s), 7.1–7.8 (3H, m), 10.8 (2H, broad s).

MASS: 340 (M+), 310, 226, 198 (Base), 170.

Elemental analysis Calcd. for $C_{14}H_{18}Cl_2N_4O_2S$: C 44.57, H 4.81, N 14.85. Found: C 44.32, H 4.52, N 14.84.

(18) 5-Chloro-3-[(4-nitroso-1-piperazinyl)carbonylmethyl]-2-benzoxazolinone mp: 212°-215° C. (dec.).

IR (Nujol): 1775, 1660 $cm^{-1}$.

NMR (DMSO-$d_6$, δ): 3.3–4.1 (6H, m), 4.2–4.7 (2H, m), 4.93 (2H, s), 7.13 (1H, dd, J=7.5 Hz and 2 Hz), 7.38 (1H, d, J=7.5 Hz), 7.45 (1H, d, J=2 Hz).

(19) 4-Chloro-3-[(4-nitroso-1-piperazinyl)carbonylmethyl]-2-benzothiazolinone mp: 179°-180° C.

IR (Nujol): 1695, 1675 $cm^{-1}$.

NMR (DMSO-$d_6$, δ): 3.5–4.1 (6H, m), 4.2–4.6 (2H, m), 5.28 (2H, s), 7.15 (1H, dd, J=7.5 Hz), 7.38 (1H, dd, J=7.5 Hz, 2 Hz), 7.68 (1H, dd, J=7.5 Hz and 2 Hz).

(20) 6-Chloro-3-[(4-nitroso-1-piperazinyl)carbonylmethyl]-2-benzothiazolinone mp: 177°-179° C.

IR (Nujol): 1685, 1650 $cm^{-1}$.

NMR (DMSO-$d_6$, δ): 3.5–4.1 (6H, m), 4.2–4.6 (2H, m), 5.00 (2H, s), 7.2–7.5 (2H, m), 7.80 (1H, d, J=20 Hz).

(21) 7-Chloro-3-[(4-nitroso-1-piperazinyl)carbonylmethyl]-2-benzothiazolinone mp: 227°-230° C. (dec.).

IR (Nujol): 1690, 1650 $cm^{-1}$.

NMR (DMSO-$d_6$, δ): 3.4–4.0 (6H, m), 4.1–4.5 (2H, m), 5.00 (2H, s), 7.1–7.5 (3H, m).

(22) 5-Methyl-3-[(4-nitroso-1-piperazinyl)carbonylmethyl]-2-benzothiazolinone mp: 214°-217° C.

IR (Nujol): 1680, 1650 $cm^{-1}$

NMR (DMSO-$d_6$, δ): 2.35 (3H, s), 3.5–4.1 (6H, m), 4.2–4.6 (2H, m), 4.97 (2H, s), 7.02 (1H, d, J=8 Hz), 7.07 (1H, s), 7.50 (1H, d, J=8 Hz).

(23) 5-Trifluoromethyl-3-[(4-nitroso-1-piperazinyl)carbonylmethyl]-2-benzothiazolinone mp: 216°-218° C.

IR (Nujol): 1690, 1650 $cm^{-1}$.

NMR (DMSO-$d_6$, δ): 3.5–4.1 (6H, m), 4.3–4.7 (2H, m), 5.15 (2H, s), 7.60 (1H, d, J=8 Hz), 7.73 (1H, s), 8.00 (1H, d, J=8 Hz).

(24) 5-Chloro-3-[(4-nitroso-1-homopiperazinyl)carbonylmethyl]-2-benzothiazolinone mp: 171°–172° C.

IR (Nujol): 1680, 1650 $cm^{-1}$

NMR ($CDCl_3$, δ): 1.8–2.3 (2H, m), 3.4–4.1 (6H, m), 4.3–4.8 (4H, m), 6.9–7.5 (3H, m).

(25) 5-Chloro-3-[(3-methyl-4-nitroso-1-piperazinyl)carbonylmethyl]-2-benzothiazolinone mp: 193°–194° C.

IR (Nujol): 1680, 1650 $cm^{-1}$.

NMR (DMSO-$d_6$, 60° C., δ): 1.07 and 1.47 (3H, 2d, J=7 Hz), 3.1–4.4 (5H, m), 4.4–4.9 (2H, m), 4.95 (2H, s), 7.15 (1H, dd, J=8 Hz and 2 Hz), 7.31 (1H, d, J=2 Hz), 7.59 (1H, d, J=8 Hz)

(26) 5-Chloro-6-phenyl-3-[(4-nitroso-1-piperazinyl)carbonylmethyl]-2-benzothiazolinone mp: 263°–266° C.

IR (Nujol): 1680, 1660 $cm^{-1}$.

(27) 5-Chloro-6-bromo-3-[(4-nitroso-1-piperazinyl)carbonylmethyl]-2-benzothiazolinone mp: >260° C.

IR (Nujol): 1680, 1590 $cm^{-1}$.

(28) 5-Chloro-3-[(4-nitroso-1-piperazinyl)carbonylmethyl]-2-benzothiazolinone mp: 212°–214° C.

IR (Nujol): 1670, 1590 $cm^{-1}$.

(29) 5-Chloro-3-[(4-amino-1-piperazinyl)carbonylmethyl]-2-benzoxazolinone hydrochloride mp: 240°–242° C. (dec.).

IR (Nujol): 2650, 2600, 1775, 1650, 1600, 1540, 1250, 1030, 935, 810, 690 $cm^{-1}$.

NMR (DMSO-$d_6$, δ): 2.8–3.2 (4H, m), 3.5–3.8 (4H, m), 4.90 (2H, s), 7.15 (1H, dd, J=9 Hz and 2 Hz), 7.38 (1H, d, J=9 Hz), 7.45 (1H, d, J=2 Hz), 9.4–10.4 (1H, broad s).

MASS (m/e): 310 (M+), 182, 71 (base).

Analysis Calcd. for $C_{13}H_{15}ClN_4O_3$.HCl. C 44.97, H 4.64, N 16.14. Found: C 44.74, H 4.97, N 16.08.

(30) 4-Chloro-3-[(4-amino-1-piperazinyl)carbonylmethyl]-2-benzothiazolinone hydrochloride mp: 237°–251° C. (dec.).

IR (Nujol): 2760, 2700, 2610, 1665, 1630 $cm^{-1}$.

NMR (DMSO-$d_6$, δ): 2.8–3.2 (4H, m), 3.5–3.9 (4H, m), 5.21 (2H, s), 7.18 (1H, dd, J=7.5 Hz), 7.38 (1H, dd, J=7.5 Hz and 2.0 Hz), 7.70 (1H, dd, J=7.5 Hz and 2 Hz), 9.5–10.3 (3H, broad s).

MASS (m/e): 326 (M+), 226, 198 (Base), 170, 71.

Analysis Calcd. for $C_{13}H_{15}ClN_4O_2S$.HCl C 42.98, H 4.44, N 15.42. Found: C 42.93, H 4.69, N 15.52.

(31) 6-Chloro-3-[(4-amino-1-piperazinyl)carbonylmethyl]-2-benzothiazolinone hydrochloride mp: 215°–243° C. (dec.).

IR (Nujol): 2700, 2600, 1670, 1650 $cm^{-1}$.

NMR (DMSO-$d_6$, δ): 2.9–3.3 (4H, m), 3.5–3.8 (4H, m), 4.99 (2H, s), 7.25 (1H, d, J=8 Hz), 7.42 (1H, dd, J=8 Hz and 2 Hz), 7.82 (1H, d, J=2 Hz), 9.2–10.5 (3H, br s).

MASS (m/e): 326 (M+), 198, 170, 71, 36 (Base).

Analysis Calcd. for $C_{13}H_{15}ClN_4O_2S.HCl.\frac{1}{2}H_2O$. C 41.94, H 4.60, N 15.05. Found: C 41.75, H 4.46, N 15.19.

(32) 7-Chloro-3-[(4-amino-1-piperazinyl)carbonylmethyl]-2-benzothiazolinone hydrochloride mp: 233°–242° C. (dec.).

IR (Nujol): 2750–2600, 1690, 1670 $cm^{-1}$.

NMR (DMSO-$d_6$, δ): 2.8–3.2 (4H, m), 3.4–3.8 (4H, m), 5.00 (2H, s), 7.1–7.5 (3H, m), 9.2–9.9 (3H, broad s).

MASS (m/e): 326 (M+, base).

Analysis Calcd for $C_{13}H_{15}ClN_4O_2S$.HCl. C 42.98, H 4.44, N 15.42. Found: C 42.57, H 4.65, N 15.38.

(33) 5-Methyl-3-[(4-amino-1-piperazinyl)carbonylmethyl]-2-benzothiazolinone hydrochloride mp: 230°–240° C. (dec.).

IR (Nujol): 2750, 2670, 2610, 1670, 1645 $cm^{-1}$.

NMR (DMSO-$d_6$, δ): 2.34 (3H, s), 2.8–3.2 (4H, m), 3.4–3.8 (4H, m), 4.92 (2H, s), 7.00 (1H, d, J=7.5 Hz), 7.04 (1H, s), 7.49 (1H, d, J=7.5 Hz), 9.3–10.3 (3H, broad s).

MASS (m/e): 306 (M+), 206, 178, 150, 71 (Base).

Analysis Calcd. for $C_{14}H_{18}N_4O_2S$.HCl. C 49.05, H 5.59, N 16.34. Found: C 49.13, H 5.61, N 16.46.

(34) 5-Trifluoromethyl-3-[(4-amino-1-piperazinyl)carbonylmethyl]-2-benzothiazolinone hydrochloride mp: 250°–260° C. (dec.).

IR (Nujol): 2750, 2670, 1690, 1655 $cm^{-1}$.

NMR (DMSO-$d_6$, δ): 2.8–3.2 (4H, m), 3.5–3.8 (4H, m), 5.07 (2H, s), 7.48 (1H, d, J=7.5 Hz), 7.60 (1H, s), 7.87 (1H, d, J=7.5 Hz), 9.3–9.9 (3H, broad s).

MASS (m/e): 360 (M+), 204, 71 (Base).

Analysis Calcd. for $C_{14}H_{15}F_3N_4O_2S.HCl.\frac{1}{2}H_2O$. C 41.44, H 4.22, N 13.81. Found: C 41.51, H 4.45, N 13.81.

(35) 5-Chloro-3-[(4-amino-1-homopiperazinyl)carbonylmethyl]-2-benzothiazolinone hydrochloride.

mp: 228°–232° C.

IR (Nujol): 3280, 3160, 2570, 1710, 1660, 1620, 1590, 1180, 1080, 900, 800 $cm^{-1}$.

NMR (DMSO-$d_6$, δ): 1.8–2.3 (2H, m), 2.9–3.9 (8H, m), 4.95 (2H, s), 7.25 (1H, dd, J=8 Hz and 2 Hz), 7.48 (1H, d, J=2 Hz), 7.71 (1H, d, J=8 Hz), 8.8–10.5 (3H, broad s).

Analysis Calcd. for $C_{14}H_{17}ClN_4O_2S$.HCl. C 44.57, H 4.81, N 14.85. Found: C 44.91, H 4.87, N 14.92.

(36) 5-Chloro-3-[(4-amino-3-methyl-1-piperazinyl)carbonylmethyl]-2-benzothiazolinone hydrochloride mp: 168°–170° C.

IR (Nujol): 3400, 2670, 2600, 1680, 1655 $cm^{-1}$.

NMR (DMSO-$d_6$, 60° C., δ): 1.22 (3H, d, J=5 Hz), 2.7–3.6 (5H, m), 3.8–4.2 (2H, m), 4.94 (2H, s), 7.15 (1H, dd, J=8 Hz and 2 Hz), 7.33 (1H, d, J=2 Hz), 7.58 (1H, d, J=8 Hz), 8.0–10.0 (3H, broad s).

Analysis Calcd. for $C_{14}H_{17}ClN_4O_2S.HCl.H_2O$. C 42.54, H 5.10, N 14.17. Found: C 42.97, H 5.12, N 13.80.

(37) 5-Chloro-6-phenyl-3-[(4-amino-1-piperazinyl)carbonylmethyl]-2-benzothiazolinone hydrochloride mp: >270° C.

IR (Nujol): 2700, 2600, 1690, 1655, 1600, 1535, 1460, 1260, 1245, 1175, 1075, 990 $cm^{-}$.

NMR (DMSO-$d_6$, δ): 2.9–3.3 (4H, m), 3.6–3.9 (4H, m), 5.07 (2H, s), 7.5–7.8 (7H, m), 9.8 (3H, br s).

(38) 5-Chloro-6-bromo-3-[(4-amino-1-piperazinyl)carbonylmethyl]-2-benzothiazolinone hydrochloride mp: 263°–265° C. (dec.).

IR (Nujol): 2650, 2600, 1705, 1660, 1590, 1520, 1470, 1380, 1350, 1310, 1240, 1190, 1070, 990 $cm^{-1}$.

NMR (DMSO-$d_6$, δ): 2.8–3.3 (4H, m), 3.5–3.9 (4H, m), 5.00 (2H, s), 7.70 (1H, s), 8.17 (1H, s), 9.7 (3H, br s).

(39) 5-Chloro-3-{[4-[N-(p-nitrobenzyloxycarbonyl)acetimidoylamino]-1-piperazinyl]carbonylmethyl}-2-benzothiazolinone IR (Film): 3300, 1750, 1695, 1680, 1660, 1630, 1590, 1520 $cm^{-1}$.

NMR (DMSO-$d_6$, δ): 2.1–2.9 (7H, m), 3.4–3.8 (4H, m), 4.95 (2H, s), 5.50 (2H, s), 7.1–7.8 (5H, m), 8.1–8.4 (3H, m).

(40) 5-Chloro-3-[(4-acetimidoylamino-1-piperazinyl)-carbonylmethyl]-2-benzothiazolinone hydrochloride mp: 194°-200° C.

IR (Nujol): 3400, 1695, 1660, 1595, 1470 $cm^{-1}$.

NMR (DMSO-$d_6$, δ): 2.16 (3H, s), 2.6–3.1 (4H, m), 3.5–4.0 (4H, m), 5.01 (2H, s), 7.2–7.8 (3H, m), 8.77 (1H, s), 9.56 (1H, s), 11.52 (1H, s).

MASS (m/e): 368 ($M^+$, base), 334, 198.

Analysis Calcd. for $C_{15}H_{19}N_5Cl_2O_2S.\frac{3}{5}H_2O$: C 43.28, H 4.92, N 16.82. Found: C 43.18, H 5.26, N 16.58.

(41) 5-Chloro-3-[(4-amidino-1-piperazinyl)carbonylmethyl]-2-benzothiazolinone hemisulfate mp: 282°-285° C. (dec.).

IR (Nujol): 3350, 3070, 1705, 1660, 1610 $cm^{-1}$.

NMR (DMSO-$d_6$, δ): 3.3–4.0 (8H, m), 4.97 (2H, s), 7.19 (1H, dd, J=7.5 Hz and 2 Hz), 7.43 (1H, d, J=2 Hz), 7.62 (1H, d, J=7.5 Hz), 7.9–9.0 (4H, broad s).

Analysis Calcd. for $C_{14}H_{16}ClN_5O_2S.\frac{1}{2}H_2SO_4$. C 41.74, H 4.25, N 17.38. Found: C 41.29, H 4.44, N 17.34.

(42) 6-Chloro-3-[(4-amino-1-piperazinyl)carbonylmethyl]-2-iminobenzothiazoline mp: 137°-142° C. (dec.).

IR (Nujol): 3250, 1655, 1610, 1585, 1240, 1160, 1025, 960, 800 $cm^{-1}$.

NMR ($CDCl_3$, δ): 2.58 (4H, t, J=5 Hz), 3.64 (4H, t, J=5 Hz), 4.70 (2H, s), 6.75 (1H, d, J=8 Hz), 7.10 (1H, dd, J=2 Hz and 8 Hz), 7.15 (1H, d, J=2 Hz).

MASS (m/e): 325 ($M^+$), 309 (base), 225.

(43) 6-Nitro-3-[(4-amino-1-piperazinyl)carbonylmethyl]-2-benzothiazolinone hydrochloride mp: 240°-242° C.

IR (Nujol): 2700, 2600, 1680, 1650, 1605, 1590, 1515, 1460, 1380, 1340, 1250, 1195, 895 $cm^{-1}$.

NMR (DMSO-$d_6$, δ): 2.9–3.9 (8H, m), 5.13 (2H, s), 7.50 (1H, d, J=9 Hz), 8.30 (1H, dd, J=9 Hz, 3 Hz), 8.77 (1H, d, J=3 Hz), 9.8 (3H, br s).

(44) 6-Chloro-1-[(4-amino-1-piperazinyl)carbonylmethyl]-3-hydroxyimino-2-indolinone hydrochloride mp: 209°-214° C.

IR (Nujol): 2600, 1715, 1640, 1610, 1380, 1270, 1250, 1200, 1100, 1040, 1025 $cm^{-1}$.

NMR (DMSO-$d_6$, δ): 2.8–3.3 (4H, m), 3.4–3.80 (4H, m), 4.77 (2H, s), 7.13 (1H, d, J=8 Hz), 7.20 (1H, s), 7.97 (1H, d, J=8 Hz).

MASS (m/e): 337 ($M^+$), 320 (base peak).

EXAMPLE 25

To a solution of hydroxylamine hydrochloride (25.2 g) in a mixed solvent of acetonitrile (300 ml) and 6N-hydrochloric acid (150 ml), was added 5-chloro-3-[(4-benzylideneamino-1-piperazinyl)carbonylmethyl]-2-benzothiazolinone (15 g). The resulting solution was stirred overnight at room temperature. After stirring for five hours under ice cooling, the crystalline precipitates were filtered, and washed successively with water (30 ml) and methylene chloride (75 ml). This product was suspended in water (30 ml) and then filtered to give 5-chloro-3-[(4-amino-1-piperazinyl)carbonylmethyl]-2-benzothiazolinone hydrochloride (8.60 g).

mp: 261°-263° C.

IR (Nujol): 2740, 2650, 2570, 2070, 1670, 1640, 1590, 1535, 1465, 1350, 1250, 1100, 805 $cm^{-1}$.

NMR ($D_2O$, δ): 3.0–3.3 (4H, m), 3.6–4.0 (4H, m), 4.93 (2H, s), 7.0–7.6 (3H, m).

Elemental analysis Calcd. for $C_{13}H_{15}ClN_4O_2S.HCl$: C 42.98, H 4.44, N 15.42. Found: C 43.14, H 4.68, N 15.54.

EXAMPLE 26

To a solution of hydroxylamine hydrochloride (3.2 g) in a mixed solvent of acetonitrile (40 ml) and 6N-hydrochloric acid (20 ml) was added 5-chloro-3-{[4-(2-hydroxybenzylideneamino)-1-piperazinyl]carbonylmethyl}-2-benzothiazolinone (2 g). The resulting solution was stirred overnight at room temperature. After stirring for five hours under ice cooling, the crystalline precipitates were filtered, and washed successively with water (4 ml) and methylene chloride (10 ml). This product was further washed by suspending in water (4 ml) and filtered to give 5-chloro-3-[(4-amino-1-piperazinyl)-carbonylmethyl]-2-benzothiazolinone hydrochloride (1.0 g)

mp: 261°-263° C.

IR (Nujol): 2740, 2650, 2570, 2070, 1670, 1640, 1590, 1535, 1465, 1350, 1250, 1100, 805 $cm^{-1}$.

NMR ($D_2O$, δ): 3.0–3.3 (4H, m), 3.6–4.0 (4H, m), 4.93 (2H, s), 7.0–7.6 (3H, m).

Elemental analysis Calcd. for $C_{13}H_{15}ClN_4O_2S.HCl$: C 42.98, H 4.44, N 15.42. Found: C 43.14, H 4.68, N 15.54.

EXAMPLE 27

To a solution of hydroxylamine hydrochloride (5.48 g) in a mixed solvent of acetonitrile (60 ml) and 6N-hydrochloric acid (30 ml) was added 5-chloro-3-[(4-isobutylideneamino-1-piperazinyl)carbonylmethyl]-2-benzothiazolinone (3.0 g). The resulting solution was stirred overnight at room temperature. After stirring for five hours under ice cooling, the crystalline precipitates were filtered, and washed successively with water (6 ml) and methylene chloride (15 ml). This product was further washed by suspending in water (6 ml) and filtered to give 5-chloro-3-[(4-amino-1-piperazinyl)carbonylmethyl]-2-benzothiazolinone hydrochloride (1.93 g).

mp: 261°-263° C.

IR (Nujol): 2740, 2650, 2570, 2070, 1670, 1640, 1590, 1535, 1465, 1350, 1250, 1100, 805 $cm^{-1}$.

NMR ($D_2O$, δ): 3.0–3.3 (4H, m), 3.6–4.0 (4H, m), 4.93 (2H, s), 7.0–7.6 (3H, m).

Elemental analysis Calcd. for $C_{13}H_{15}ClN_4O_2S.HCl$: C 42.98, H 4.44, N 15.42. Found: C 43.14, H 4.68, N 15.54.

EXAMPLE 28

In a similar manner to that of Example 25, 26 or 27, there were obtained the following compounds.

(1) 6-Chloro-3-[(4-amino-1-piperazinyl)carbonylmethyl]-2-iminobenzothiazoline mp: 137°-142° C. (dec.).

IR (Nujol): 3250, 1655, 1610, 1585, 1240, 1160, 1025, 960, 800 $cm^{-1}$.

NMR ($CDCl_3$, δ): 2.58 (4H, t, J=5 Hz), 3.64 (4H, t, J=5 Hz), 4.70 (2H, s), 6.75 (1H, d, J=8 Hz), 7.10 (1H, dd, J=2 Hz, 8 Hz), 7.15 (1H, d, J=2 Hz).

MASS (m/e): 325 ($M^+$), 309 (base), 225.

(2) 6-Nitro-3-[(4-amino-1-piperazinyl)carbonylmethyl]-2-benzothiazolinone hydrochloride mp: 240°-242° C.

IR (Nujol): 2700, 2600, 1680, 1650, 1605, 1590, 1515, 1460, 1380, 1340, 1250, 1195, 895 $cm^{-1}$.

NMR (DMSO-$d_6$, δ): 2.9–3.9 (8H, m), 5.13 (2H, s), 7.50 (1H, d, J=9 Hz), 8.30 (1H, dd, J=9 Hz, 3 Hz), 8.77 (1H, d, J=3 Hz), 9.8 (3H, br s).

(3) 5-Chloro-3-[(4-amino-1-piperazinyl)carbonylmethyl]-2-benzoxazolinone hydrochloride mp: 240°-242° C. (dec.).

IR (Nujol): 2650, 2600, 1775, 1650, 1600, 1540, 1250, 1030, 935, 810, 690 $cm^{-1}$.

NMR (DMSO-$d_6$, δ): 2.8–3.2 (4H, m), 3.5–3.8 (4H, m), 4.90 (2H, s), 7.15 (1H, dd, J=9 Hz and 2 Hz), 7.38 (1H, d, J=9 Hz), 7.45 (1H, d, J=2 Hz), 9.4–10.4 (1H, broad s).

MASS (m/e): 310 (M+), 182, 71 (base)

Analysis Calcd. for $C_{13}H_{15}ClN_4O_3.HCl$: C 44.97, H 4.64, N 16.14. Found: C 44.74, H 4.97, N 16.08.

(4) 4-Chloro-3-[(4-amino-1-piperazinyl)carbonylmethyl]-2-benzothiazolinone hydrochloride.

mp: 237°-251° C. (dec.).

IR (Nujol): 2760, 2700, 2610, 1665, 1630 $cm^{-1}$.

NMR (DMSO-$d_6$, δ): 2.8–3.2 (4H, m), 3.5–3.9 (4H, m), 5.21 (2H, s), 7.18 (1H, dd, J=7.5 Hz), 7.38 (1H, dd, J=7.5 Hz and 2.0 Hz), 7.70 (1H, dd, J=7.5 Hz, 2 Hz), 9.5–10.3 (3H, broad s).

MASS (m/e): 326 (M+), 226, 198 (base), 170, 71.

Analysis Calcd. for $C_{13}H_{15}ClN_4O_2S.HCl$: C 42.98, H 4.44, N 15.42. Found: C 42.93, H 4.69, N 15.52.

(5) 6-Chloro-3-[(4-amino-1-piperazinyl)carbonylmethyl]-2-benzothiazolinone hydrochloride mp: 215°-243° C. (dec.).

IR (Nujol): 2700, 2600, 1670, 1650 $cm^{-1}$.

NMR (DMSO-$d_6$, δ): 2.9–3.3 (4H, m), 3.5–3.8 (4H, m), 4.99 (2H, s), 7.25 (1H, d, J=8 Hz), 7.42 (1H, dd, J=8 Hz and 2 Hz), 7.82 (1H, d, J=2 Hz), 9.2–10.5 (3H, br s).

MASS (m/e): 326 (M+), 198, 170, 71, 36 (base).

Analysis Calcd. for $C_{13}H_{15}ClN_4O_2S.HCl.\frac{1}{2}H_2O$: C 41.94, H 4.60, N 15.05. Found: C 41.75, H 4.46, N 15.19.

(6) 7-Chloro-3-[(4-amino-1-piperazinyl)carbonylmethyl]-2-benzothiazolinone hydrochloride mp: 233°-242° C. (dec.).

IR (Nujol): 2750–2600, 1690, 1670 $cm^{-1}$.

NMR (DMSO-$d_6$, δ): 2.8–3.2 (4H, m), 3.4–3.8 (4H, m), 5.00 (2H, s), 7.1–7.5 (3H, m), 9.2–9.9 (3H, broad s).

MASS (m/e): 326 (M+, base).

Analysis Calcd. for $C_{13}H_{15}ClN_4O_2S.HCl$: C 42.98, H 4.44, N 15.42. Found: C 42.57, H 4.65, N 15.38.

(7) 5-Methyl-3-[(4-amino-1-piperazinyl)carbonylmethyl]-2-benzothiazolinone hydrochloride mp: 230°-240° C. (dec.).

IR (Nujol): 2750, 2670, 2610, 1670, 1645 $cm^{-1}$.

NMR (DMSO-$d_6$, δ): 2.34 (3H, s), 2.8–3.2 (4H, m), 3.4–3.8 (4H, m), 4.92 (2H, s), 7.00 (1H, d, J=7.5 Hz), 7.04 (1H, s), 7.49 (1H, d, J=7.5 Hz), 9.3–10.3 (3H, broad s).

MASS (m/e): 306 (M+), 206, 178, 150, 71 (base).

Analysis Calcd. for $C_{14}H_{18}N_4O_2S.HCl$: C 49.05, H 5.59, N 16.34. Found: C 49.13, H 5.61, N 16.46.

(8) 5-Trifluoromethyl-3-[(4-amino-1-piperazinyl)carbonylmethyl]-2-benzothiazolinone hydrochloride mp: 250°-260° C. (dec.).

IR (Nujol): 2750, 2670, 1690, 1655 $cm^{-1}$.

NMR (DMSO-$d_6$, δ): 2.8–3.2 (4H, m), 3.5–3.8 (4H, m), 5.07 (2H, s), 7.48 (1H, d, J=7.5 Hz), 7.60 (1H, s), 7.87 (1H, d, J=7.5 Hz), 9.3–9.9 (3H, broad s).

MASS (m/e): 360 (M+), 204, 71 (base)

Analysis Calcd. for $C_{14}H_{15}F_3N_4O_2S.HCl.\frac{1}{2}H_2O$: C 41.44, H 4.22, N 13.81. Found: C 41.51, H 4.45, N 13.81.

(9) 5-Chloro-3-[(4-amino-1-homopiperazinyl)carbonylmethyl]-2-benzothiazolinone hydrochloride mp: 228°-232° C.

IR (Nujol): 3280, 3160, 2570, 1710, 1660, 1620, 1590, 1180, 1080, 900, 800 $cm^{-1}$.

NMR (DMSO-$d_6$, δ): 1.8–2.3 (2H, m), 2.9–3.9 (8H, m), 4.95 (2H, s), 7.25 (1H, dd, J=8 Hz and 2 Hz), 7.48 (1H, d, J=2 Hz), 7.71 (1H, d, J=8 Hz), 8.8–10.5 (3H, broad s).

Analysis Calcd. for $C_{14}H_{17}ClN_4O_2S.HCl$: C 44.57, H 4.81, N 14.85. Found: C 44.91, H 4.87, N 14.92.

(10) 5-Chloro-3-[(4-amino-3-methyl-1-piperazinyl)carbonylmethyl]-2-benzothiazolinone hydrochloride mp: 168°-170° C.

IR (Nujol): 3400, 2670, 2600, 1680, 1655 $cm^{-1}$.

NMR (DMSO-$d_6$, 60° C., δ): 1.22 (3H, d, J=5 Hz), 2.7–3.6 (5H, m), 3.8–4.2 (2H, m), 4.94 (2H, s), 7.15 (1H, dd, J=8 Hz and 2 Hz), 7.33 (1H, d, J=2 Hz), 7.58 (1H, d, J=8 Hz), 8.0–10.0 (3H, broad s).

Analysis Calcd. for $C_{14}H_{17}ClN_4O_2S.HCl.H_2O$: C 42.54, H 5.10, N 14.17. Found: C 42.97, H 5.12, N 13.80.

(11) 5-Chloro-6-phenyl-3-[(4-amino-1-piperazinyl)carbonylmethyl]-2-benzothiazolinone hydrochloride mp: >270° C.

IR (Nujol): 2700, 2600, 1690, 1655, 1600, 1535, 1460, 1260, 1245, 1175, 1075, 990 $cm^{-1}$.

NMR (DMSO-$d_6$, δ): 2.9–3.3 (4H, m), 3.6–3.9 (4H, m), 5.07 (2H, s), 7.5–7.8 (7H, m), 9.8 (3H, br s).

(12) 5-Chloro-6-bromo-3-[(4-amino-1-piperazinyl)carbonylmethyl]-2-benzothiazolinone hydrochloride mp: 263°-265° C. (dec.).

IR (Nujol): 2650, 2600, 1705, 1660, 1590, 1520, 1470, 1380, 1350, 1310, 1240, 1190, 1070, 990 $cm^{-1}$.

NMR (DMSO-$d_6$, δ): 2.8–3.3 (4H, m), 3.5–3.9 (4H, m), 5.00 (2H, s), 7.70 (1H, s), 8.17 (1H, s), 9.7 (3H, br s).

(13) 6-Chloro-2-oxo-1-[(4-amino-1-piperazinyl)carbonylmethyl]-1,2-dihydrothiazolo[5,4-b]pyridine hydrochloride mp: 238°-246° C. (dec.).

IR (Nujol): 2700, 2600, 1690, 1640, 1580, 1535, 1410, 1260, 1200 $cm^{-1}$.

NMR (DMSO-$d_6$, δ): 3.04 (4H, m), 3.63 (4H, broad s), 5.07 (2H, s), 8.02 (1H, d, J=2 Hz), 8.38 (1H, d, J=2 Hz), 9.90 (3H, broad s).

MASS: 327 (M+), 227, 199, 171, 71 (Base).

Elemental analysis Calcd. for $C_{12}H_{14}ClN_5O_2S.HCl$: C 39.57, H 4.15, N 19.23. Found: C 39.82, H 4.02, N 19.38.

(14) 3-[(4-Amino-1-piperazinyl)carbonylmethyl]-2-benzothiazolinone hydrochloride mp: 249°-258° C. (dec.).

IR (Nujol): 2750, 2700, 2620, 2080, 1670, 1640, 1610, 1545, 1260, 760 $cm^{-1}$.

NMR (DMSO-$d_6$, δ): 2.8–3.3 (4H, m), 3.3–3.9 (4H, m), 4.95 (2H, s), 7.0–7.5 (3H, m), 7.63 (1H, dd, J=2 Hz and 7.5 Hz), 9.0–10.5 (3H, broad s).

Elemental analysis Calcd. for $C_{13}H_{16}N_4O_2S.HCl$: C 47.49, H 5.21, N 17.04. Found: C 47.54, H 5.02, N 17.14.

EXAMPLE 29

In a similar manner to that of Example 15, there were obtained the following compounds.

(1) 5-Chloro-3-[(4-benzylideneamino-1-piperazinyl)carbonylmethyl]-2-benzothiazolinone mp: 213°-215° C.

IR (Nujol): 1700 (sh), 1680, 1650, 1590 $cm^{-1}$.

NMR (DMSO-$d_6$, δ): 2.87–3.47 (4H, m), 3.47–3.93 (4H, m), 5.00 (2H, s), 7.10–7.87 (9H, m)

(2) 6-Chloro-1-[(4-benzylideneamino-1-piperazinyl)carbonylmethyl]-2,3-indolinedione mp: 241°-243° C.

IR (Nujol): 1755, 1735, 1665, 1620, 1375, 1255, 1130, 1100, 1000 $cm^{-1}$.

(3) 6-Chloro-3-[(4-benzylideneamino-1-piperazinyl)carbonylmethyl]-2-iminobenzothiazoline mp: 158°-160° C. (dec.).

IR (Nujol): 3350, 1625, 1575, 990, 800, 750 $cm^{-1}$.

(4) 5-Chloro-3-{[4-(2-hydroxybenzylideneamino)-1-piperazinyl]carbonylmethyl}-2-benzothiazolinone mp: 206°-207° C.

IR (Nujol): 1690, 1660, 1590 $cm^{-1}$.

NMR (DMSO-$d_6$, δ): 3.0-3.5 (4H, m), 3.5-4.1 (4H, m), 5.00 (2H, s), 7.3-7.8 (8H, m), 11.07 (1H, s).

(5) 5-Chloro-3-[(4-isobutylideneamino-1-piperazinyl)-carbonylmethyl]-2-benzothiazolinone mp: 147°-149° C.

IR (Nujol): 1690, 1650, 1590 $cm^{-1}$.

NMR ($CDCl_3$, δ): 1.05 (6H, d, J=7 Hz), 2.45 (1H, sepl, J=7 Hz), 3.00 (4H, m), 3.73 (4H, m), 4.70 (2H, s), 6.87-7.43 (4H, m).

(6) 6-Nitro-3-[(4-benzylideneamino-1-piperazinyl)carbonylmethyl]-2-benzothiazolinone.

mp: 248°-250° C.

IR (Nujol): 1690, 1660, 1460, 1340, 1250, 1140, 990 $cm^{-1}$.

EXAMPLE 30

A mixture of 6-chloro-1-[(4-benzylideneamino-1-piperazinyl)carbonylmethyl]-2,3-indolinedione (1.5 g) and hydroxylamine hydrochloride (2.5 g) in acetonitrile (100 ml), conc. hydrochloric acid (50 ml), and water (50 ml) was heated at 40° C. for 2 hour. The reaction mixture was concentrated up to 20 ml and the precipitates appeared were filtered, and air-dried. This crude material was recrystallized from aqueous methanol at first, and for water finally to give 6-chloro-1-[(4-amino-1-piperazinyl)carbonylmethyl]-3-hydroxyimino-2-indolinone hydrochloride (0.54 g).

mp: 209°-214° C.

IR (Nujol): 2600, 1715, 1640, 1610, 1380, 1270, 1250, 1200, 1100, 1040, 1025 $cm^{-1}$.

NMR (DMSO-$d_6$, δ): 2.8-3.3 (4H, m), 3.4-3.8 (4H, m), 4.77 (2H, s), 7.13 (1H, d, J=8 Hz), 7.20 (1H, s), 7.97 (1H, d, J=8 Hz).

MASS (m/e): 337 (M+), 320 (base peak).

What we claim is:

1. A compound of the formula:

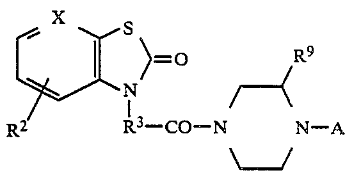

wherein $R^2$ is halogen, $R^3$ is lower alkylene, $R^9$ is hydrogen or lower alkyl, X is CH or N, and A is hydrogen, a group of the formula:

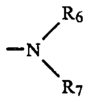

wherein $R^6$ and $R^7$ are each hydrogen, lower alkanoyl or lower alkaneimidoyl, or a group of the formula: $-N=R^8$ wherein $R^8$ is lower alkylidene, or a pharmaceutical acceptable salt thereof.

2. A compound of claim 1, wherein $R^2$ is chlorine, $R^3$ is methylene, and $R^9$ is hydrogen or methyl, A is hydrogen, a group of the formula:

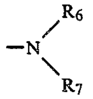

wherein $R^6$ and $R^7$ are each hydrogen, formyl or acetimidoyl, or a group of the formula: $-N=R^8$ wherein $R^8$ is methylene.

3. A compound of claim 2, wherein $R^9$ is hydrogen, X is CH and

A is amino.

4. A compound of claim 3, which is 5-chloro-3-[(4-amino-1-piperazinyl)carbonylmethyl]-2-benzothiazolinone or its hydrochloride.

5. An antithrombotic pharmaceutical composition comprising, as an active ingredient, an effective amount of a compound of claim 1 or pharmaceutically acceptable salt thereof in association with pharmaceutically acceptable carrier or excipient.

6. A method for the treatment of thrombosis in a human being or animal comprising administering an effective amount of a compound of claim 1 or pharmaceutically acceptable salt thereof.

* * * * *